(12) United States Patent
Schieber et al.

(10) Patent No.: US 12,011,390 B2
(45) Date of Patent: Jun. 18, 2024

(54) LACRIMAL DRUG DELIVERY DEVICE

(71) Applicant: THE REGENTS OF THE UNIVERSITY OF COLORADO, A BODY CORPORATE, Denver, CO (US)

(72) Inventors: Andrew Schieber, Laguna Niguel, CA (US); Linda Thai, Mission Viejo, CA (US); Malik Kahook, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 69 days.

(21) Appl. No.: 17/524,610

(22) Filed: Nov. 11, 2021

(65) Prior Publication Data
US 2022/0062037 A1 Mar. 3, 2022

Related U.S. Application Data

(63) Continuation of application No. 16/302,514, filed as application No. PCT/US2017/033277 on May 18, 2017, now Pat. No. 11,207,211.
(Continued)

(51) Int. Cl.
*A61F 9/00* (2006.01)
*A61K 9/00* (2006.01)
*A61K 45/00* (2006.01)

(52) U.S. Cl.
CPC .......... *A61F 9/0008* (2013.01); *A61K 9/0051* (2013.01); *A61K 45/00* (2013.01)

(58) Field of Classification Search
CPC ............................ A61F 9/0008; A61K 9/0051
See application file for complete search history.

(56) References Cited

U.S. PATENT DOCUMENTS

| 3,817,248 A | 6/1974 | Buckles |
| 3,828,777 A | 8/1974 | Ness |

(Continued)

FOREIGN PATENT DOCUMENTS

| CA | 2829533 | 8/2006 |
| CN | 201469516 | 5/2010 |

(Continued)

OTHER PUBLICATIONS

Fleisher et al., "Improved oral drug delivery: solubility limitations overcome by the use of prodrugs", Advanced Drug Delivery Reviews, 1996, vol. 19, No. 2, pp. 115-130.
(Continued)

*Primary Examiner* — William R Carpenter
(74) *Attorney, Agent, or Firm* — Polsinelli PC

(57) ABSTRACT

A lacrimal drug delivery device includes a reservoir configured to hold a drug. The reservoir is moveable between a relaxed state and an expanded state. A connector is fluidly coupled to the reservoir and a lumen is formed in the connector wherein the drug is configured to flow from the reservoir to an delivery site through the lumen. A hydrogel is within the lumen and configured to absorb the drug from the reservoir and deliver the drug from the lumen at the delivery site. The hydrogel includes a first section which absorbs the drug at a first rate of absorption. A delivery guide is detachably coupled to the reservoir to deliver the reservoir into a lacrimal sac of a patient.

20 Claims, 15 Drawing Sheets

Related U.S. Application Data

(60) Provisional application No. 62/339,258, filed on May 20, 2016.

(56) References Cited

U.S. PATENT DOCUMENTS

| | | | |
|---|---|---|---|
| 3,962,414 | A | 6/1976 | Michaels |
| 4,468,816 | A | 9/1984 | Kaufer |
| 4,658,816 | A | 4/1987 | Ector, Jr. |
| 4,781,675 | A | 11/1988 | White |
| 5,219,334 | A | 6/1993 | Tsukada |
| 5,318,513 | A | 6/1994 | Leib |
| 5,410,016 | A | 4/1995 | Hubbell |
| 5,437,625 | A | 8/1995 | Kurihashi |
| 5,836,935 | A | 11/1998 | Ashton |
| 6,152,916 | A | 11/2000 | Bige |
| 6,196,993 | B1 | 3/2001 | Cohan |
| 6,217,896 | B1 | 4/2001 | Benjamin |
| 6,344,047 | B1 | 2/2002 | Price |
| 6,881,198 | B2 | 4/2005 | Brown |
| 7,066,904 | B2 | 6/2006 | Rosenthal |
| 8,034,370 | B2 | 10/2011 | Shiah |
| 8,409,606 | B2 | 4/2013 | Sawhney |
| 8,563,027 | B2 | 10/2013 | Jarrett |
| 10,993,834 | B2 * | 5/2021 | Kahook ............ A61F 9/00772 |
| 2003/0014036 | A1 | 1/2003 | Varner |
| 2003/0114791 | A1 | 6/2003 | Rosenthal |
| 2007/0298075 | A1 | 12/2007 | Borgia |
| 2008/0086101 | A1 * | 4/2008 | Freilich ............... A61F 9/0017 604/294 |
| 2008/0181930 | A1 | 7/2008 | Rodstrom |
| 2008/0199510 | A1 | 8/2008 | Ruane |
| 2009/0104243 | A1 | 4/2009 | Utkhede |
| 2009/0187098 | A1 | 7/2009 | Makower |
| 2009/0306608 | A1 | 12/2009 | Li |
| 2010/0034870 | A1 | 2/2010 | Sim et al. |
| 2010/0179468 | A1 | 7/2010 | Becker |
| 2010/0274204 | A1 | 10/2010 | Rapacki |
| 2011/0251568 | A1 | 10/2011 | Beeley |
| 2011/0301555 | A1 | 12/2011 | Gonzalez-Zugasti |
| 2011/0311606 | A1 | 12/2011 | Coldren |
| 2011/0311607 | A1 | 12/2011 | Coldren |
| 2012/0095439 | A1 | 4/2012 | de Juan, Jr. |
| 2013/0023837 | A1 | 1/2013 | Becker |
| 2013/0172268 | A1 | 7/2013 | Jarrett |
| 2013/0220346 | A1 | 8/2013 | Lust |
| 2013/0289467 | A1 * | 10/2013 | Haffner ............... A61K 9/2072 604/290 |
| 2014/0296834 | A1 * | 10/2014 | Moss .................. A61P 19/10 604/285 |
| 2014/0364891 | A1 | 12/2014 | Mendius et al. |
| 2015/0351961 | A1 | 12/2015 | Kahook |
| 2018/0344524 | A1 * | 12/2018 | Kahook ............... A61M 37/00 |
| 2019/0125581 | A1 | 5/2019 | Heitzmann |

FOREIGN PATENT DOCUMENTS

| | | |
|---|---|---|
| EP | 1891942 | 3/2010 |
| JP | 2006525953 | 11/2006 |
| JP | 2009532133 | 9/2009 |
| JP | 2009544355 | 12/2009 |
| JP | 2012046530 | 3/2012 |
| JP | 2012515628 | 7/2012 |
| JP | 2015109990 | 6/2015 |
| JP | 2016508064 | 3/2016 |
| TW | 201212962 | 4/2012 |
| WO | WO0071062 | 11/2000 |
| WO | WO02056863 | 7/2002 |
| WO | WO2004062649 | 7/2004 |
| WO | WO2006122165 | 11/2006 |
| WO | WO2008024982 | 2/2008 |
| WO | WO2008043905 | 4/2008 |
| WO | WO2009032328 | 3/2009 |
| WO | WO2010085696 | 7/2010 |
| WO | WO2010092735 | 8/2010 |
| WO | WO2014113384 | 7/2014 |
| WO | WO2017091404 | 6/2017 |

OTHER PUBLICATIONS

Mooberry et al., "Tubercidin stabilizes microtubules against vinblastine-induced depolymerization, a taxol-like effect", Cancer Letters, 1995, vol. 96, No. 2, pp. 261-266.

Murube et al., "Subcutaneous abdominal artificial tears pump-reservoir for severe dry eyes," Orbit, 2003, vol. 22, No. 1, p. 29.

Ro et al., "Morphological and degradation studies of sirolimus-containing poly(lactide-co-glycolide) discs," Journal of Biomedical Materials Research Part B: Applied Biomaterials, 2012, vol. 100B, No. 3, pp. 767-777.

Smith et al., "A sensitive assay for taxol and other microtubule-stabilizing agents," Cancer Letters, 1994, vol. 79, No. 2, pp. 213-219.

* cited by examiner

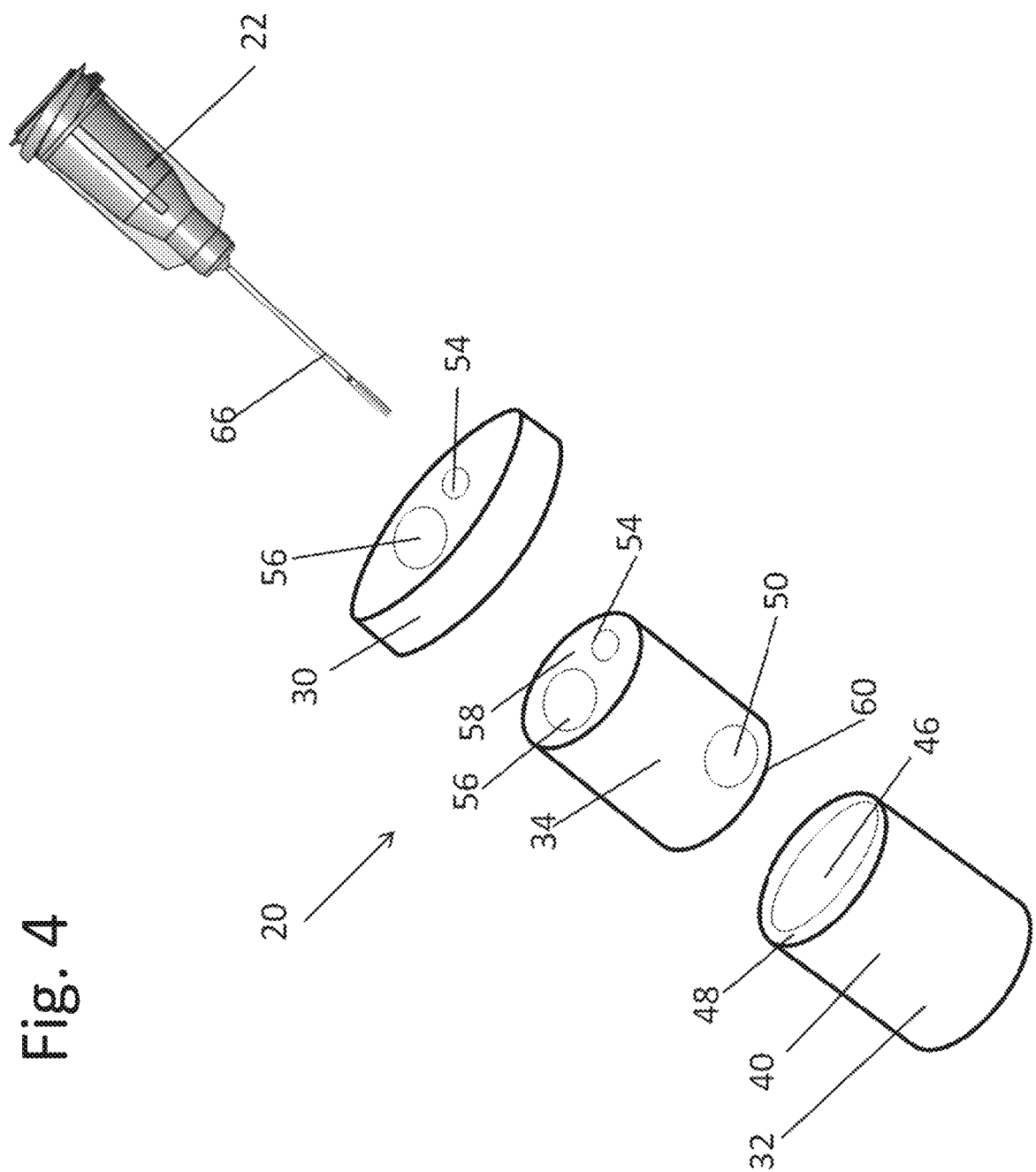

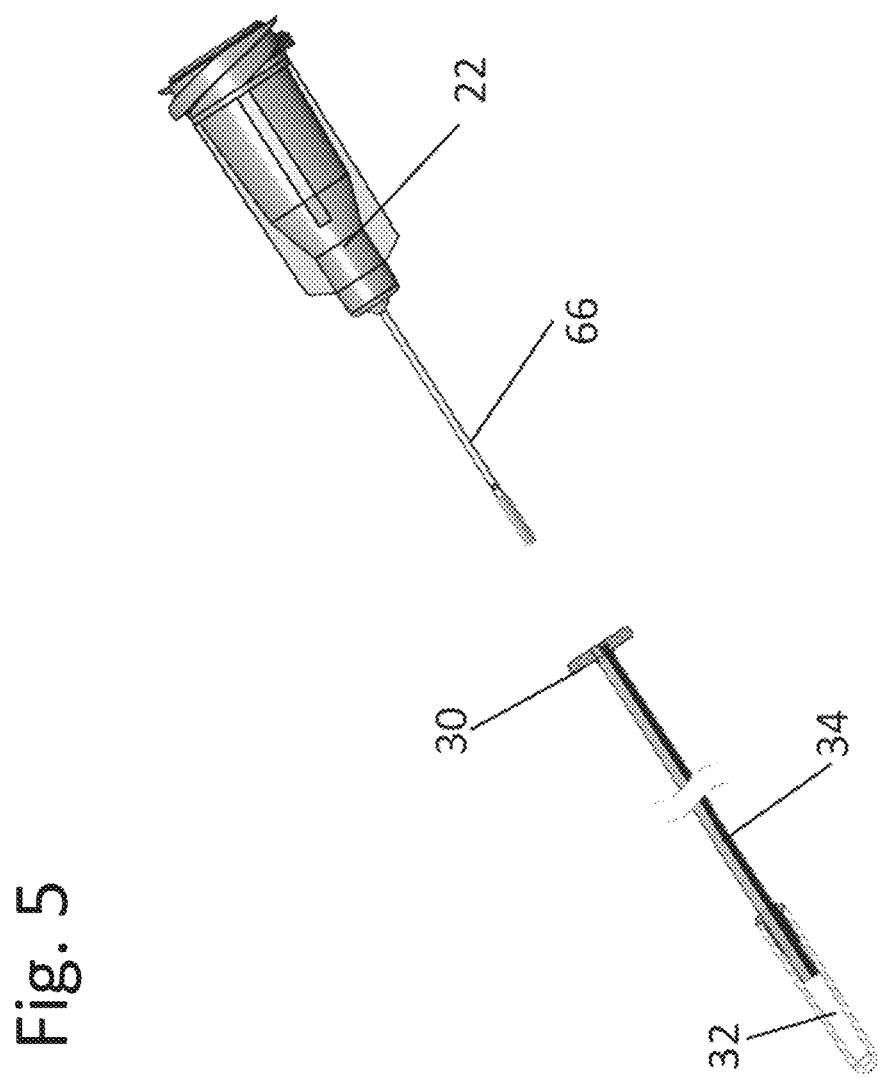

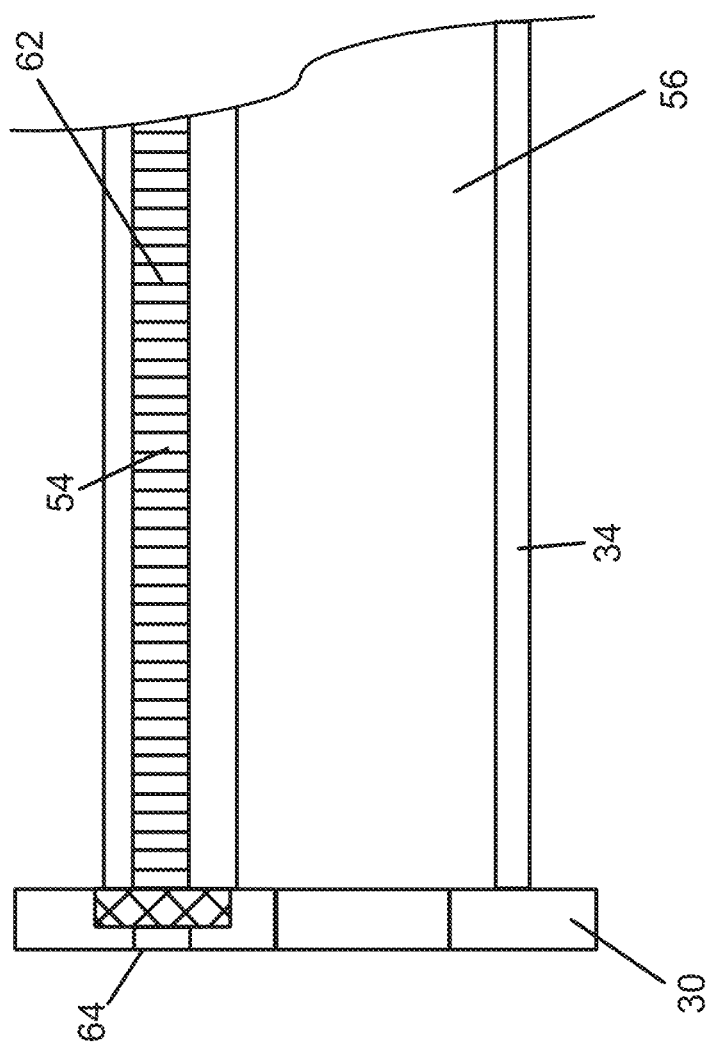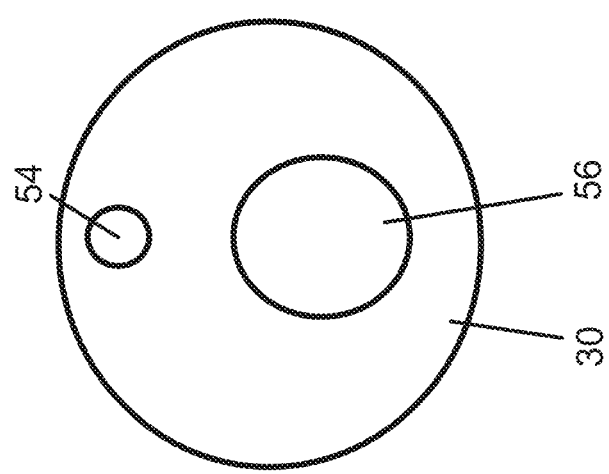

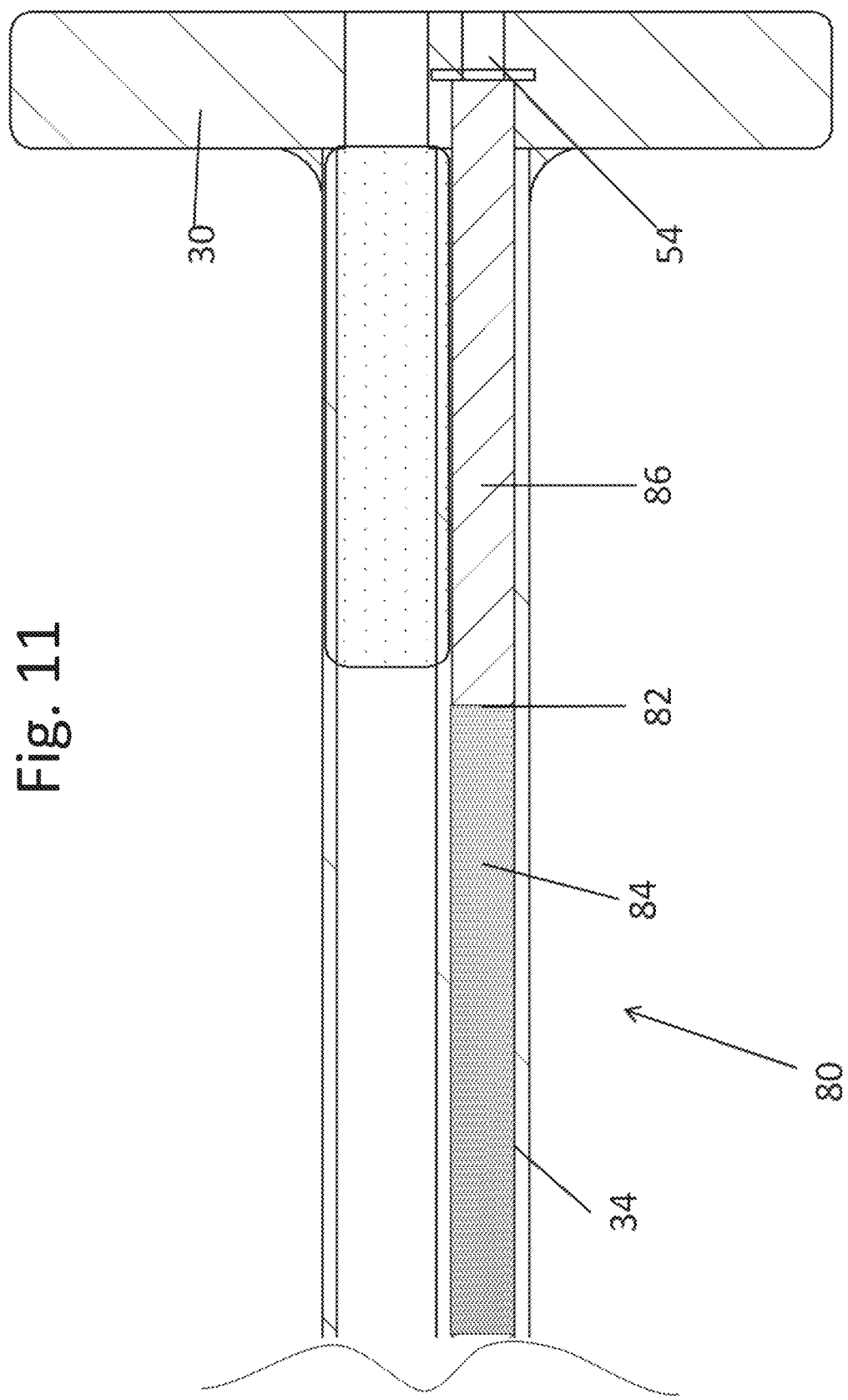

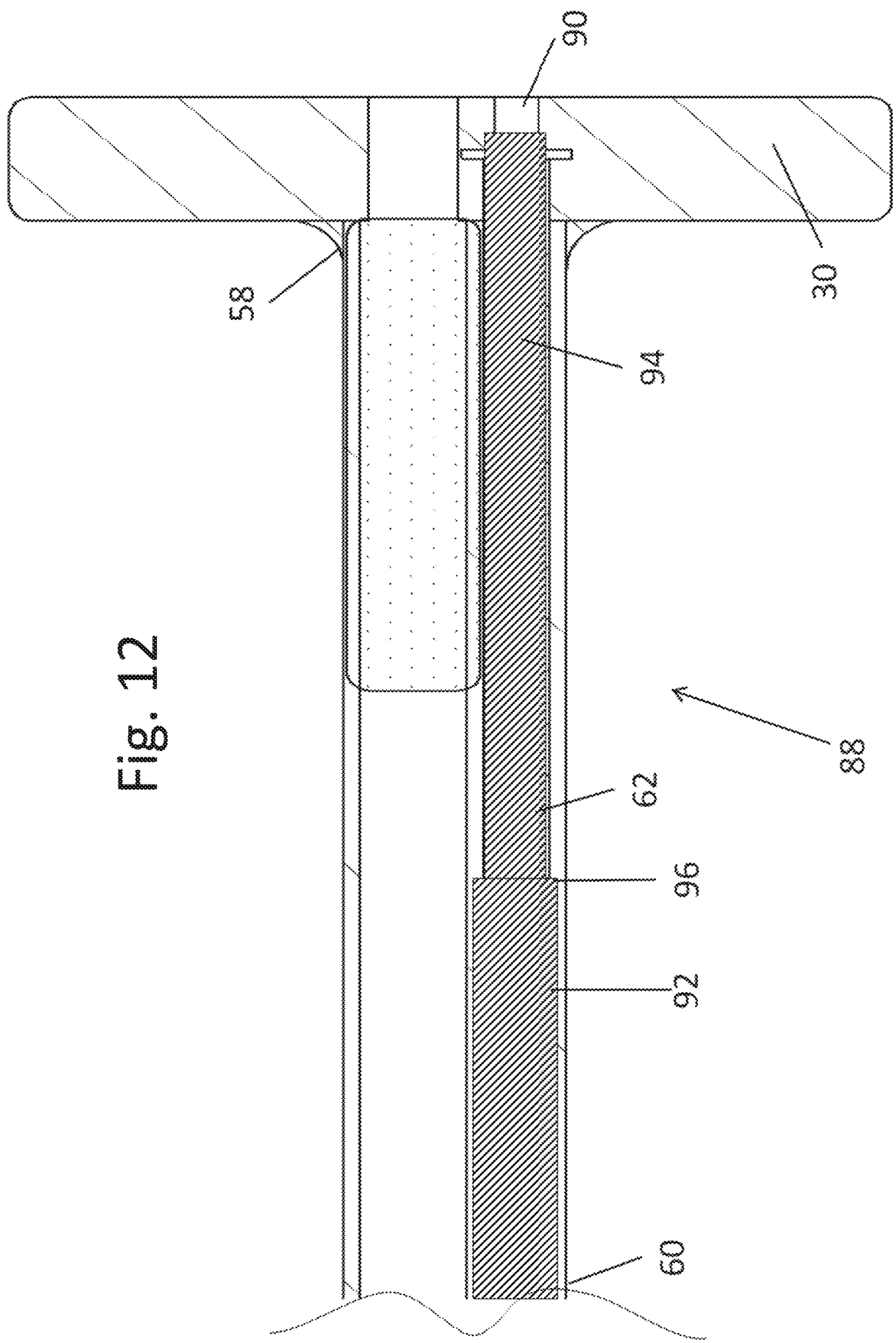

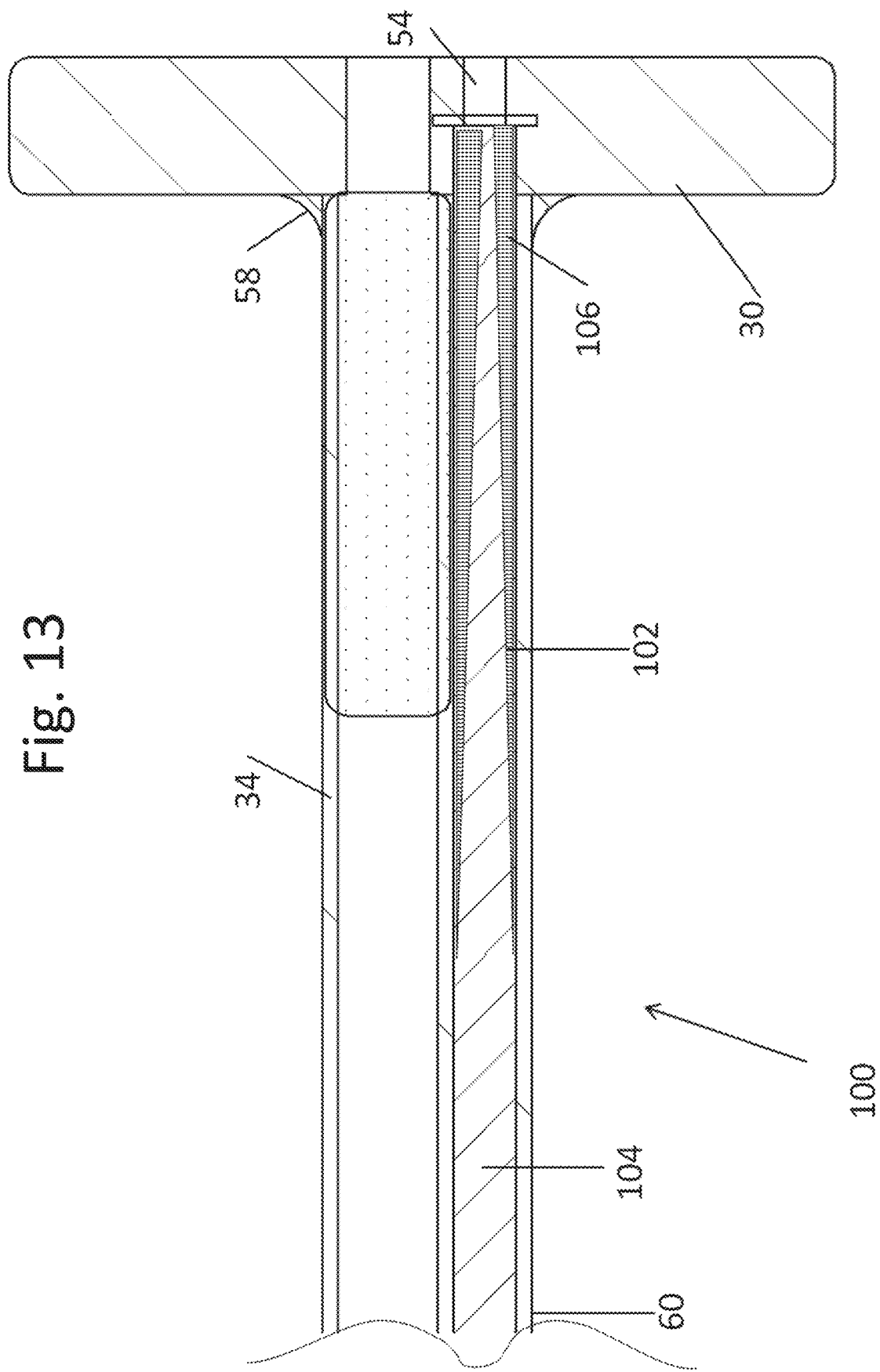

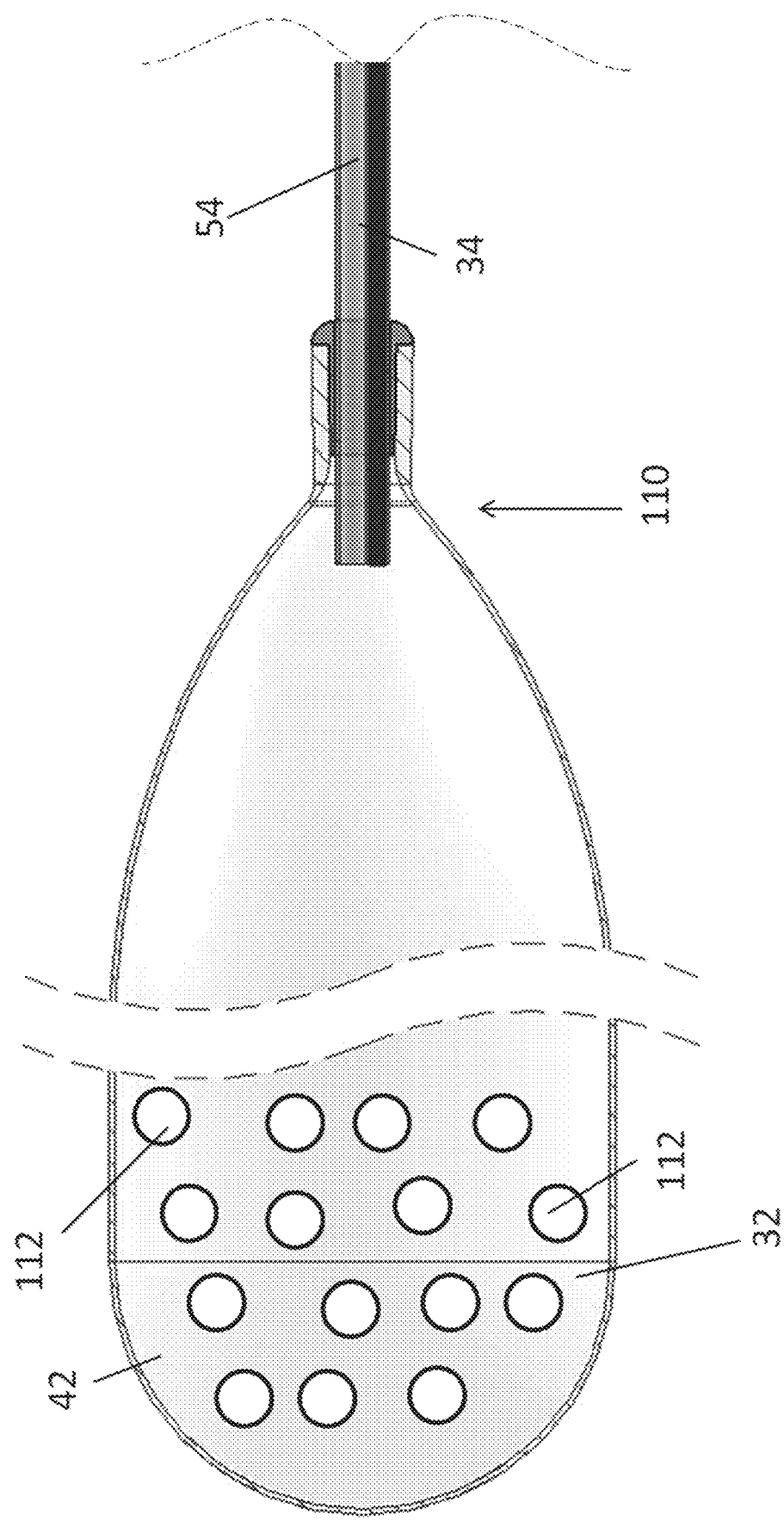

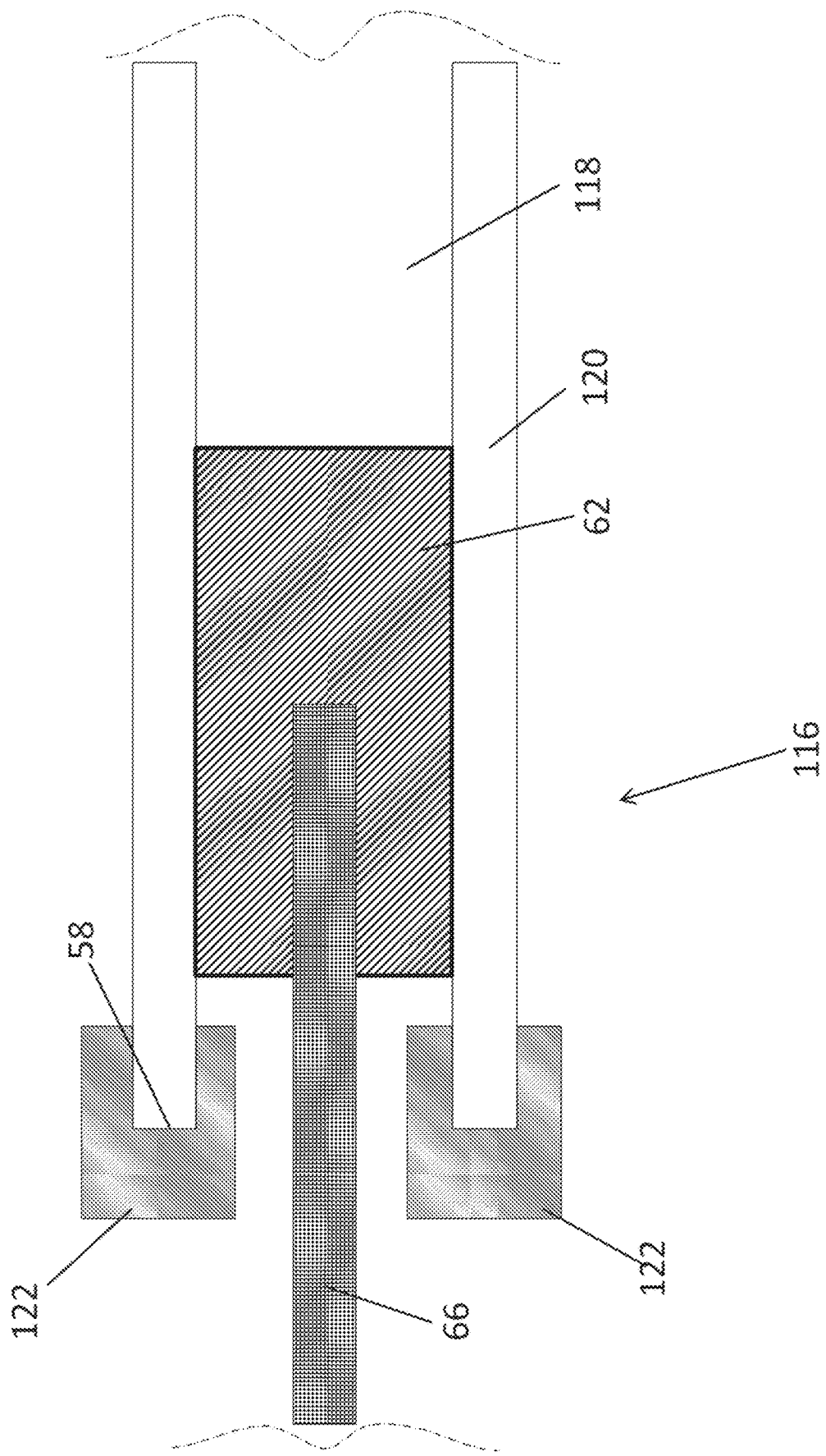

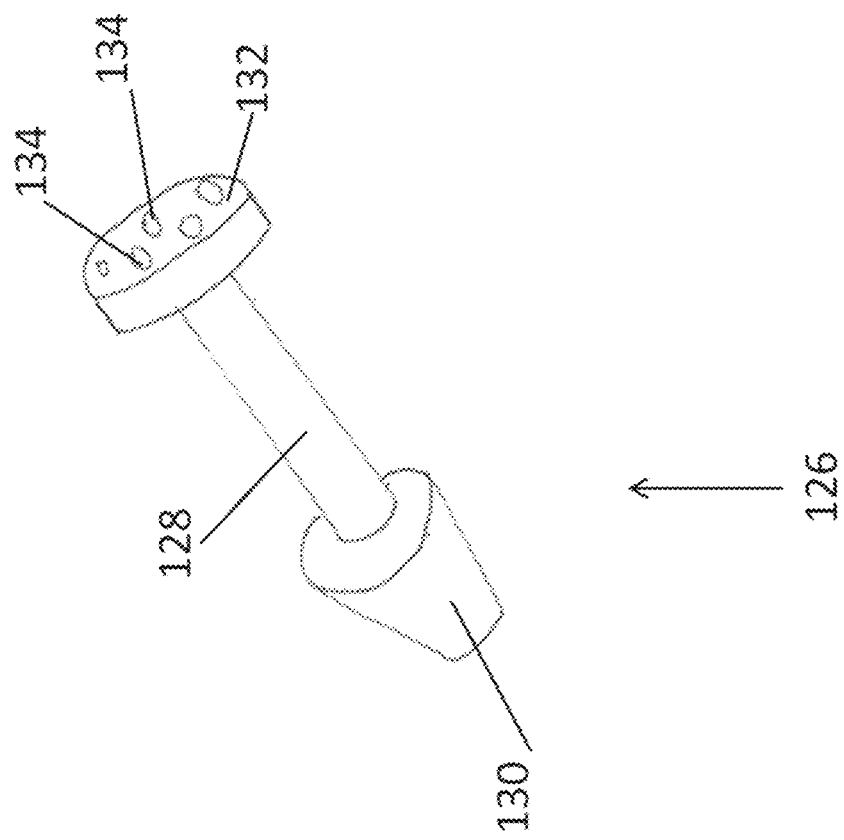

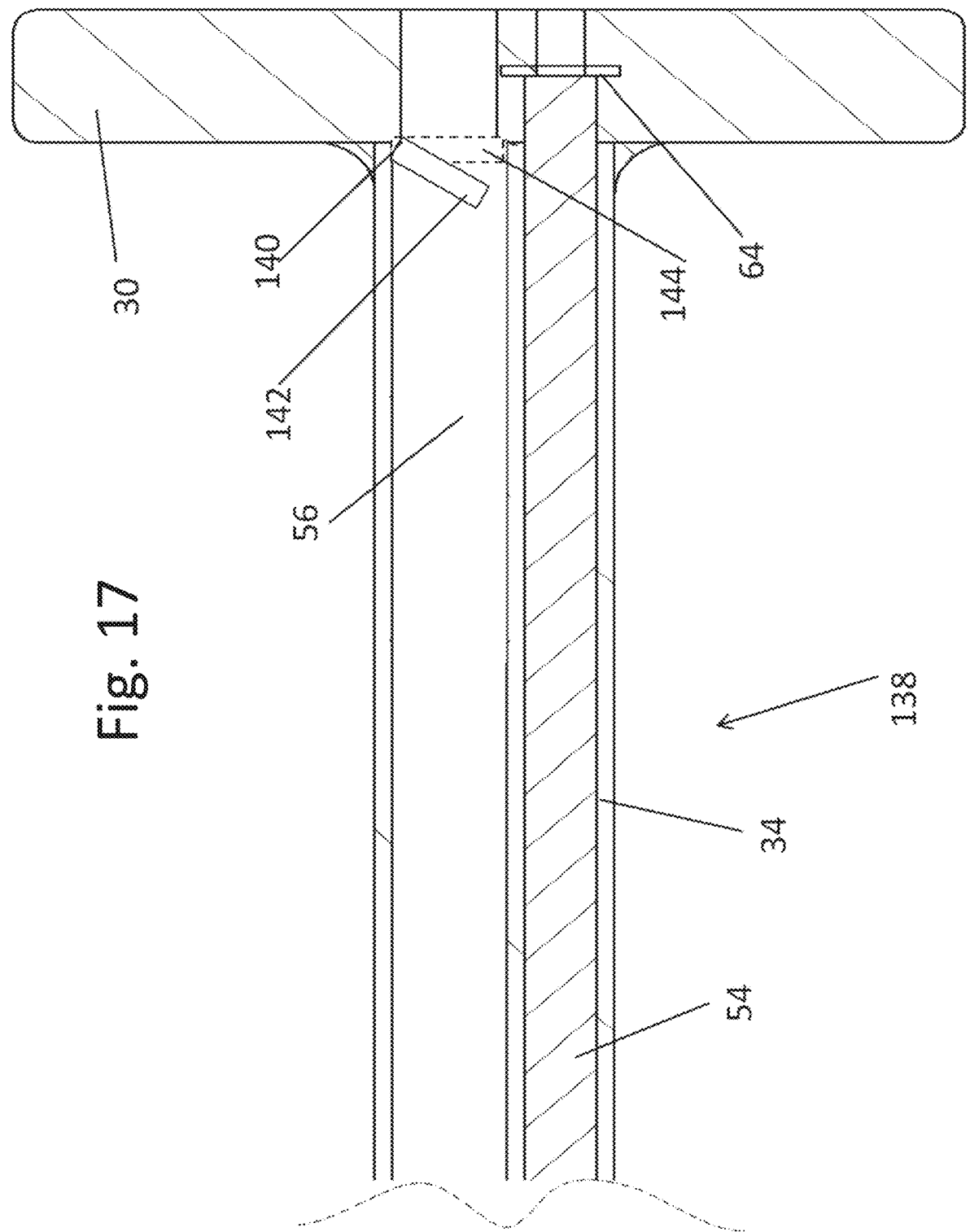

LACRIMAL DRUG DELIVERY DEVICE

CROSS-REFERENCE TO RELATED APPLICATIONS

This U.S. Continuation Application claims priority to U.S. application Ser. No. 16/302,514, filed on Nov. 16, 2018, now allowed which Application claims priority to International Application No. PCT/US2017/033277, filed on May 18, 2017, which claims priority to U.S. Provisional Patent Application No. 62/339,258, filed on May 20, 2016. These applications are hereby incorporated by reference in their entirety for all purposes.

FIELD OF THE INVENTION

The present invention generally relates to a medicament delivery device and, more particularly, to an implantable drug delivery device for delivering a drug to the eye through the lacrimal duct.

BACKGROUND OF THE INVENTION

Ocular diseases and disorders frequently require the introduction of medicament into the eye for the treatment of symptoms. Conventional means for delivering the medicament include topical application of the medicament to the surface of the eye such as through the use of eye drops. Eye drops are typically applied repeatedly by the user either according to a defined schedule or when discomfort develops. However, there are several drawbacks with manual application of eye drops. Users do not always adhere to the prescribed schedule. There may also be waste of the drug associated with the application as users may use a larger volume of the drug than may be absorbed by the eye in a timely manner or may not accurately place the drops inside the eye.

Installing a drug releasing implant into the punctum can overcome some of the problems associated with manual installation of the medicament. A punctal plug is one implantable device that is inserted into the punctum and releases medicament into the eye. However, several drawbacks are associated with this type of device as well. The device may become dislodged if the user rubs their eye area or sneezes. The device may block the natural flow of tears into the lacrimal system. The device holds a limited volume of medicament which requires the devices to be replaced. The device also fails to provide an even distribution rate of the medicament. Instead, a large amount of the medicament is dispersed when the device is first implanted and the delivery rate tapers over time.

Other types of lacrimal drug delivery implants are described in International Application No. PCT/US2014/011477 and published as WO 2014113384, the disclosure of which is hereby incorporated by reference herein in its entirety. However, such lacrimal implants still need to accurately control the rate of delivery of the drug.

Therefore, it is desirable to provide an improved drug delivery implant that provides long term consistent release of medicament to the delivery site.

BRIEF SUMMARY OF THE INVENTION

The present invention generally relates to a medicament delivery device and, more particularly, to an implantable drug delivery device for delivering a drug to the eye through the lacrimal duct.

In one embodiment, the invention contemplates a lacrimal drug delivery device, comprising: a reservoir configured to hold a drug, the reservoir expandable between a relaxed state and an expanded state; a connector fluidly coupled to the reservoir, a lumen formed in the connector wherein the drug is configured to flow from the reservoir to a delivery site through the lumen; a hydrogel within the lumen, the hydrogel being configured to absorb the drug from the reservoir and deliver the drug from the lumen at the drug at the delivery site, the hydrogel including a first section which absorbs the drug at a first rate of absorption; and a delivery guide detachably coupled to the reservoir to deliver the reservoir into a lacrimal sac of a patient. In one embodiment, said hydrogel includes a second section which absorbs the drug at a second rate of absorption different from the first rate of absorption. In one embodiment, the first section has a first porosity and the second section has a second porosity different from the first porosity. In one embodiment, the first rate of absorption and the second rate of absorption are at least partially controlled by the porosity, wherein a larger porosity provides a faster rate of absorption. In one embodiment, the first section is adjacent the reservoir and the second section is opposite the first section, the first porosity larger than the second porosity. In one embodiment, the hydrogel includes a dry state wherein the drug is separate from the hydrogel prior to the device being implanted and a wetted state wherein the drug is absorbed by the hydrogel after the device is implanted. In one embodiment, the connector includes a second lumen with the delivery guide removably positioned within the second lumen. In one embodiment, the delivery guide comprises a guide wire. In one embodiment, the guide wire includes an opening therethrough such that the drug is delivered through the opening to transfer the reservoir from the relaxed state to the expanded state. In one embodiment, said device further comprises a valve within the second lumen which seals the second lumen when the delivery device is removed. In one embodiment, said device further comprises a filter coupled to the connector, the filter sealing the hydrogel within the lumen while allowing the drug to flow through the filter. In one embodiment, the filter prevents external substances from contaminating the hydrogel. In one embodiment, the drug is configured to elude through the hydrogel and filter and the filter at least partially controls flow of the drug. In one embodiment, the reservoir is elastic such that the reservoir exerts a compressive force on the drug when the reservoir is in the expanded state. In one embodiment, the first section and the second section have the same or substantially similar chemical formulation. In one embodiment, the first section and the second section have different formulations. In one embodiment, the first section is hydrophilic and the second section is hydrophobic. In one embodiment, the lumen includes a proximal end and a distal end and the ratio of the first section to the second section is greater at the proximal end than at the distal end. In one embodiment, the first section extends from the proximal end to the distal end such that the drug is transferred along the lumen through the first section. In one embodiment, the first section has a first thickness and the second section has a second thickness less than the first thickness such that the first section absorbs the drug faster than the second section. In one embodiment, the lumen has a distal diameter adjacent the reservoir and a proximal diameter opposite the reservoir, wherein the proximal diameter is smaller than the distal diameter. In one embodiment, the delivery site is at least one of a lacrimal punctum and nasolacrimal duct.

In one embodiment, the invention contemplates a lacrimal drug delivery device, comprising: a reservoir configured to hold a drug, the reservoir moveable between a relaxed state and an expanded state; a connector fluidly coupled to the reservoir, the connector including a first lumen, a second lumen, a proximal end, and a distal end, the drug configured to flow from the reservoir to a delivery site through the first lumen; a hydrogel within the first lumen, the hydrogel configured to absorb the drug from the reservoir and deliver the drug from the lumen at the delivery site; a delivery guide within the second lumen and configured to transfer the reservoir between the relaxed state to the expanded state, the delivery guide detachably coupled to the reservoir to position the reservoir in a lacrimal sac of a patient; and a valve within the second lumen, the valve sealing the second lumen when the delivery guide is removed and allowing the delivery guide to be reinserted to retransfer the reservoir between the relaxed state and the expanded state. In one embodiment, the delivery guide includes an opening and the drug is delivered through the opening and into the reservoir to transfer the reservoir from the relaxed state to the expanded state. In one embodiment, the hydrogel includes a first section with a first rate of absorption and a second section with a second rate of absorption different than the first rate of absorption.

In one embodiment there is a lacrimal drug delivery device including a reservoir configured to hold a drug, the reservoir moveable between a relaxed state and an expanded state; a connector fluidly coupled to the reservoir, a lumen formed in the connector wherein the drug is configured to flow from the reservoir to a delivery site through the lumen; a hydrogel within the lumen, the hydrogel being configured to absorb the drug from the reservoir and deliver the drug from the lumen at the drug delivery site, the hydrogel including a first section which absorbs the drug at a first rate of absorption; and a delivery guide detachably coupled to the reservoir to deliver the reservoir into a lacrimal sac of a patient.

In another embodiment, the hydrogel includes a second section which absorbs the drug at a second rate of absorption different than the first rate of absorption. The first section may have a first porosity and the second section may have a second porosity different from the first porosity and the rate of absorption may be at least partially controlled by the porosity, wherein a larger porosity provides a faster rate of absorption. The first section may be adjacent the reservoir and the second section opposite the first section and the first porosity may be larger than the second porosity.

In another embodiment, the hydrogel includes a dry state wherein the drug is separate from the hydrogel prior to the device being implanted and a wetted state wherein the drug is absorbed by the hydrogel after the device is implanted. In one embodiment, the connector includes a second lumen with the delivery guide removably positioned within the second lumen. In one embodiment, the delivery guide is a guide wire and may include an opening therethrough such that the drug is delivered through the opening to transfer the reservoir from the relaxed state to the expanded state.

In a further embodiment, a lacrimal drug delivery device further includes a valve within the second lumen which seals the second lumen when the delivery device is removed. In a further embodiment, a filter is coupled to the connector to seal the hydrogel within the lumen while allowing the drug to flow through the filter and may prevent external substances from contaminating the hydrogel. In one embodiment the drug is configured to elude through the hydrogel and filter and the filter at least partially controls flow of the drug. In one embodiment, the reservoir is elastic such that the reservoir exerts a compressive force on the drug when the reservoir is in the expanded state. In one embodiment, the first section and the second section have the same or substantially similar chemical formulation; in another embodiment, the first section and second section have different formulations. In one embodiment, the first section is hydrophilic and the second section is hydrophobic.

In another embodiment, the lumen includes a proximal end and a distal end and the ration of the first section to the second section is greater at the proximal end than at the distal end. In one embodiment, the first section extends from the proximal end to the distal end such that the drug is transferred along the lumen through the first section. In one embodiment, the first section has a first thickness and the second section has a second thickness less than the first thickness such that the first section absorbs the drug faster than the second section. In one embodiment the lumen has a distal diameter adjacent the reservoir and a proximal diameter opposite the reservoir, wherein the proximal diameter is smaller than the distal diameter. In one embodiment the delivery site is at least one of a lacrimal punctum and a nasolacrimal duct.

In another embodiment, there is a lacrimal drug delivery device comprising a reservoir to hold a drug, the reservoir moveable between a relaxed state and an expanded state; a connector fluidly coupled to the reservoir, the connector including a first lumen, a second lumen, a proximal end, and a distal end, the drug configured to flow from the reservoir to a delivery site through the first lumen; a hydrogel within the first lumen, the hydrogel configured to absorb the drug from the reservoir and deliver the drug from the lumen at the delivery site; a delivery guide within the second lumen and configured to transfer the reservoir from the relaxed state to the expanded state, the delivery guide detachably coupled to the reservoir to position the reservoir in a lacrimal sac of a patient; and a valve within the second lumen, the valve sealing the second lumen when the delivery device is removed and allowing the delivery device to be reinserted to retransfer the reservoir between the relaxed state and the expanded state. In one embodiment, the delivery guide includes an opening and the drug is delivered through the opening and into the reservoir to transfer the reservoir from the relaxed state to the expanded state. In one embodiment, the hydrogel includes a first section with a first rate of absorption and a second section with a second rate of absorption different than the first rate of absorption.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "patient" or "subject" refers to any living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Prevention" or "preventing" as used herein, includes, but is not limited to: (1) inhibiting the onset of a disease in a subject or patient which may be at risk and/or predisposed to the disease, wherein such inhibition may be either partial or complete, but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the terms "medication" or "therapeutic agent" refer to any compound and/or molecule that treats or prevents or alleviates the symptoms of disease or condition, including, but not limited to, a drug or pharmaceutical composition. Medication is considered to be delivered or present in therapeutically effective amounts or pharmaceutically effective amounts.

"Therapeutically effective amounts" or "pharmaceutically effective amounts", as used herein, means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, treatment may also merely reduce symptoms, improves (to some degree) and/or delays disease progression among other effects. It is not intended that treatment be limited to instances wherein a disease or affliction is cured. It is sufficient that symptoms are reduced.

As used herein, the terms "medical device," "implant," "device," "medical device," "medical implant," "implant/device," and the like are used synonymously to refer to any object that is designed to be placed partially or wholly within a patient's body for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. While medical devices are normally composed of biologically compatible synthetic materials (e.g., medical-grade stainless steel, nitinol, titanium and other metals; exogenous polymers, such as polyurethane, silicone, PLA, PLGA, PGA, PCL), other materials may also be used in the construction of the medical implant. While not limiting the present invention to any particular device, specific medical devices and implants that are particularly relevant to this invention include stents, punctal plugs, Crawford tubes, catheters, lacrimal tubes, ocular or other shunts, and drug delivery systems. In some embodiments, the device incorporates a contrast material or opaque materials that allow for visualization with standard imaging devices (for example, barium to allow for x-ray visualization).

As used herein, the term "medication reservoir" refers to any elastic structure containing medication or therapeutic agent. In preferred embodiments, the reservoir is made of stretchy plastics or silicones.

As used herein, the term "proximal" refers to a location situated toward a point of origin (e.g., between a physician and a lacrimal implant device).

As used herein, the term "distal" refers to a location situated away from a point of origin (e.g., behind a lacrimal implant device relative to a physician).

As used herein, the term "hydrogel" is used to refer to an absorbing or otherwise retaining material (e.g., adsorbing material), such as super-absorbent polymers, hydrocolloids, and water-absorbent hydrophilic polymers, for example. In some examples, the term "hydrogel" refers to super-absorbent polymer particles in a "dry or dehydrated" state, more specifically, particles containing from no water up to an amount of water less than the weight of the particles, such as less than about 5%, by weight, water. In some examples, the term "hydrogel" refers to a super-absorbent polymer in the "dry or dehydrated" state when the hydrogel is not expandable and also refers to its hydrated or expanded state, more specifically, hydrogels that have absorbed at least their weight in water, such as several times their weight in water. As the hydrogel material absorbs fluid, it size can increase and its shape can change to bias against at least a portion of a lacrimal canaliculus ampulla or lacrimal canaliculus wall, for example.

As used herein, the term "medicament" refers to any active agent that is suitable for use in medical treatment, such as a medicinal compound or drug.

As used herein, the term "active agent" refers to any molecular entity that exerts an effect on a living organism.

As used herein, the term "polymer" refers to any organic macromolecule containing one or more repeating units, as is well known in the art.

As used herein, a "copolymer" refers to any polymer in which there are at least two types of repeating units included. A copolymer can be a block copolymer, in which there are segments containing multiple repeating units of one type, bonded to segments containing multiple repeating units of a second type.

As used herein, the term "hydrophilic polymer" refers to any polymer that can be wetted by water, i.e., does not have a water-repellant surface. A hydrophilic polymer can absorb water to a small degree, for example about 0-100 wt % of water, but does not greatly swell in volume as does a hydrogel-forming polymer.

As used herein, the terms "implanted" refers to having completely or partially placed a device within a host. A device is partially implanted when some of the device reaches, or extends to the outside of, a host.

As used herein, the term "steroids" refers to any organic compound that contains a core composed of twenty carbon atoms bonded together that take the form of four fused rings: three cyclohexane rings (designated as rings A, B, and C in the figure to the right) and one cyclopentane ring (the D ring). The steroids vary by the

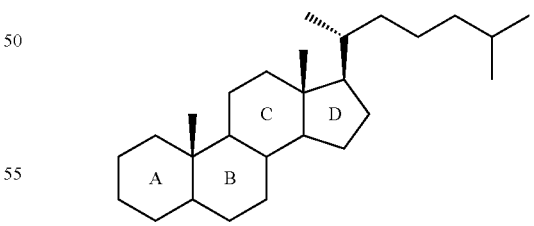

functional groups attached to this four-ring core and by the oxidation state of the rings. Examples of steroids include, but are not limited to, the dietary fat cholesterol, the sex hormones estradiol and testosterone, and the anti-inflammatory drug dexamethasone.

As used herein, the term "non-steroidal anti-inflammatory agents," "nonsteroidal anti-inflammatory drugs," usually abbreviated to NSAIDs or NAIDs, but also referred to as nonsteroidal anti-inflammatory agents/analgesics (NSAIAs)

or nonsteroidal Anti-inflammatory medicines (NSAIMs), refers to any drug with analgesic and antipyretic (fever-reducing) effects and which have, in higher doses, anti-inflammatory effects.

As used herein, the term "antibiotics" refers to any compound or substance that kills or inhibits the growth of bacteria, fungus, or other microorganism.

As used herein, the term "anti-inflammatory agent" refers to any substance or treatment that reduces inflammation.

As used herein, the term "immunosuppressant agents" refers to all drugs that inhibit or prevent activity of the immune system.

As used herein, the term "anti-neoplastic agents" refers to all drugs that prevent or inhibit the development, maturation, or spread of neoplastic cells.

As used herein, the term "prostaglandin analogues" refers to all molecules that bind to a prostaglandin receptor.

As used herein, the term "nitric oxide" or "nitrogen monoxide" refers to any binary diatomic molecule with the chemical formula NO.

As used herein, the term "endothelin" refers to any protein that consisting of 21 amino acid residues that are produced in various cells and tissues, that play a role in regulating vasomotor activity, cell proliferation, and the production of hormones, and that have been implicated in the development of vascular disease. For example, endothelin biological activity may include, but is not limited to, constrict blood vessels, raise blood pressure, decrease eye pressure, and protect neuronal tissues from degeneration.

As used herein, the term "corticosteroids" refers to a class of chemicals that includes any naturally produced steroid hormone or synthetic steroid hormone analogue. Corticosteroids are involved in a wide range of physiologic processes, including, but not limited to, stress response, immune response, and regulation of inflammation, carbohydrate metabolism, protein catabolism, blood electrolyte levels, and behavior.

As used herein, the term "antibody-based immunosuppressants" refers to any antibody (e.g., polyclonal, monoclonal, Fab etc) having an immunosuppressant activity.

As used herein, the term "release of an agent" refers to any presence of the agent, or a subcomponent thereof, emanating from an implant device.

As used herein, the terms "analogue or analog" refer to any chemical compound that is structurally similar to a parent compound but differs slightly in composition (e.g., one atom or functional group is different, added, or removed). An analogue may or may not have different chemical or physical properties than the original compound and may or may not have improved biological and/or chemical activity. For example, the analogue may be more hydrophilic, or it may have altered reactivity as compared to the parent compound. The analogue may mimic the chemical and/or biological activity of the parent compound (i.e., it may have similar or identical activity), or, in some cases, may have increased or decreased activity. The analogue may be a naturally or non-naturally occurring (e.g., recombinant) variant of the original compound. An example of an analogue is a mutein (i.e., a protein analogue in which at least one amino acid is deleted, added, or substituted with another amino acid). Other types of analogues include isomers (enantiomers, diastereomers, and the like) and other types of chiral variants of a compound, as well as structural isomers. The analogue may be a branched or cyclic variant of a linear compound. For example, a linear compound may have an analogue that is branched or otherwise substituted to impart certain desirable properties (e.g., improve hydrophilicity or bioavailability).

As used herein, the term "derivative" refers to any chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." An analogue may have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). The term "derivative" also includes conjugates, and prodrugs of a parent compound (i.e., chemically modified derivatives that can be converted into the original compound under physiological conditions). For example, the prodrug may be an inactive form of an active agent. Under physiological conditions, the prodrug may be converted into the active form of the compound. Prodrugs may be formed, for example, by replacing one or two hydrogen atoms on nitrogen atoms by an acyl group (acyl prodrugs) or a carbamate group (carbamate prodrugs). More detailed information relating to prodrugs is found, for example, in Fleisher et al., Advanced Drug Delivery Reviews 19 (1996) 115 incorporated herein by reference. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form, for example, alkali metal salts or alkaline earth metal salts (e.g., sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds that simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, the term "inhibitor" or "antagonist" refers to any agent that prevents a biological process from occurring and/or slows the rate and/or slows the degree of occurrence of a biological process. The process may be a general one such as scarring or refer to a specific biological action such as, for example, a molecular process resulting in release of a cytokine.

As used herein, the term "agonist" refers to any agent that stimulates a biological process or rate or degree of occurrence of a biological process. The process may be a general one such as scarring or refer to a specific biological action such as, for example, a molecular process resulting in release of a cytokine.

As used herein, the term "anti-microtubule agent" should be understood to include any protein, peptide, chemical, or other molecule that impairs the function of microtubules, for example, through the prevention or stabilization of polymerization. Compounds that stabilize polymerization of microtubules are referred to herein as "microtubule stabilizing agents." A wide variety of methods may be utilized to determine the anti-microtubule activity of a particular compound, including for example, assays described by Smith et al. (Cancer Lett. 79(2):213-219, 1994) and Mooberry et al., (Cancer Lett. 96(2):261-266, 1995) both incorporated herein by reference.

Any concentration ranges, percentage range, or ratio range recited herein are to be understood to include concentrations, percentages or ratios of any integer within that range and fractions thereof, such as one tenth and one hundredth of an integer, unless otherwise indicated. In addition, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to both one polymer or a mixture comprising two or more polymers. As used herein, the term "about" means ±15%.

As used herein, the term "biomaterial" refers to any substance (other than drugs) or combination of substances synthetic or natural in origin, which can be used for any period of time, as a whole or as a part of a system which treats, augments, or replaces any tissue, organ, or function of the body.

As used herein, the term "biocompatibility" refers to the ability of a material to perform with an appropriate host response in a specific application.

As used herein, the term "elastic limit" or "yield strength" refers to the stress at which a material begins to deform plastically. Prior to the yield point the material will deform elastically and will return to its original shape when the applied stress is removed. Once the yield point is passed, some fraction of the deformation will be permanent and non-reversible.

As used herein, the term "elastic" refers to a material that with very large deformability when forces are applied on it with complete recoverability, meaning the object will return to its initial shape and size when these forces are removed. Such a feature has also been referred to as rubber elasticity. Molecular Requirements of such "elastic" materials: Material must consist of polymer chains, Need to change conformation and extension under stress. Polymer chains must be highly flexible. Need to access conformational changes (not w/ glassy, crystalline, stiff mat.) Polymer chains must be joined in a network structure. Need to avoid irreversible chain slippage (permanent strain). One out of 100 monomers must connect two different chains. Connections (covalent bond, crystallite, glassy domain in block copolymer) Examples of elastic polymers include rubber, latex, synthetic rubbers, neoprene, silicone and the like.

As used herein, the term "non-elastic" refers to a material that with low or no deformability when forces are applied on it. Beyond the strain limit, a non-elastic material will experience irreversible deformation. Polymer chains are not flexible and do not easily access conformational changes. These may undergo irreversible chain slippage (permanent strain) Examples include glass, hard plastics, amorphous glassy polymers and the like.

As used herein, the term "semi-elastic" refers to a material that with moderate deformability when forces are applied on it with complete recoverability, meaning the object will return to its initial shape and size when these forces are removed. There are a number of semi-elastic polymers. Examples of semi-crystalline polymers are linear polyethylene (PE), polyethylene terephthalate (PET), polytetrafluoroethylene (PTFE) or isotactic polypropylene (PP).

As used herein, the term "self-compression" refers to when a material is added to a reservoir and filled to distortion leading to elastic forces to compress material inside the reservoir. This self-compression provides a force to initiate distribution of the material within the reservoir out of the reservoir, either through a flow limiting port or through forced diffusion.

As used herein, the term "stent" refers to any artificial 'tube' inserted into a natural passage/conduit in the body to prevent, or counteract, a disease-induced, localized flow constriction. The term may also refer to a tube used to temporarily hold such a natural conduit open to allow access for surgery.

As used herein, the term "shunt" refers to any artificial 'tube' inserted into the body to create a hole or passage to allow movement of fluids between two areas. Said tube may be implanted temporarily or may be permanent.

As used herein, the term "Foley catheter" refers to a flexible tube that is often passed through the urethra and into the bladder. The tube has two separated channels, or lumens, running down its length. One lumen is open at both ends, and allows urine to drain out into a collection bag. The other lumen has a valve on the outside end and connects to a balloon at the tip; the balloon is inflated with sterile water, or other fluid/gas, when it lies inside the bladder, in order to stop it from slipping out.

As used herein, the term "catheter" refers to any tube that can be inserted into a body cavity, duct, or vessel. Catheters thereby allow drainage, administration of fluids or gases, or access by surgical instruments. The process of inserting a catheter is catheterization. In most uses, a catheter is a thin, flexible tube ("soft" catheter), though in some uses, it is a larger, solid ("hard") catheter. A catheter left inside the body, either temporarily or permanently, may be referred to as an indwelling catheter. A permanently inserted catheter may be referred to as a permcath.

As used herein, the term "microelectromechanical systems" or "MEMS" refers to technology of very small devices. MEMS are separate and distinct from the hypothetical vision of molecular nanotechnology or molecular electronics. MEMS are made up of components between 1 to 100 micrometres in size (i.e. 0.001 to 0.1 mm), and MEMS devices generally range in size from 20 micrometres (20 millionths of a metre) to a millimetre (i.e. 0.02 to 1.0 mm). They usually consist of a central unit that processes data (the microprocessor) and several components that interact with the surroundings such as microsensors.

As used herein, the term "PLGA or poly(lactic-co-glycolic acid)" refers to a copolymer and is approved for therapeutic devices by the United States Food and Drug Administration (FDA), owing to its biodegradability and biocompatibility. PLGA has been studied for slow drug release.

As used herein, the term "polyethylene glycol" (abbreviated PEG) refers to any polyether compound. For example, PEG is commercially available as polyethylene oxide (PEO) or polyoxyethylene (POE), depending on its molecular weight (Carbowax®).

BRIEF DESCRIPTION OF THE FIGURES

The foregoing summary, as well as the following detailed description of embodiments of the drug delivery device, will be better understood when read in conjunction with the appended drawings of an exemplary embodiment. It should be understood, however, that the invention is not limited to the precise arrangements and instrumentalities shown.

In the drawings:

FIG. 4 is an exploded front perspective view of the drug delivery device and delivery guide of FIG. 2.

FIG. 5 is an assembled front perspective view of the drug delivery device and delivery guide of FIG. 2.

FIG. 8 is a front view of the faceplate of FIG. 2.

FIG. 9 is a side sectional view of the faceplate and connector of FIG. 2.

FIG. 11 is a side sectional view of the faceplate and connector of FIG. 2 with hydrogel in the lumen in accordance with a second exemplary embodiment of the present invention.

FIG. 12 is a side sectional view of the faceplate and connector of FIG. 2 with hydrogel in the lumen in accordance with a third exemplary embodiment of the present invention.

FIG. 13 is a side sectional view of the faceplate and connector of FIG. 2 with hydrogel in the lumen in accordance with a fourth exemplary embodiment of the present invention.

FIG. 14 is a side sectional view of the faceplate and connector of FIG. 2 with drug containing spheres in the reservoir in accordance with a fifth exemplary embodiment of the present invention.

FIG. 15 is a side sectional view of a connector, delivery guide, and hydrogel in accordance with a sixth exemplary embodiment of the present invention.

FIG. 16 is a front perspective view of a face plate in accordance with a seventh exemplary embodiment of the present invention.

FIG. 17 is a front perspective view of a connector, face plate, hydrogel, and valve in accordance with an eighth exemplary embodiment of the present invention.

DETAILED DESCRIPTION OF THE INVENTION

Figure 1:
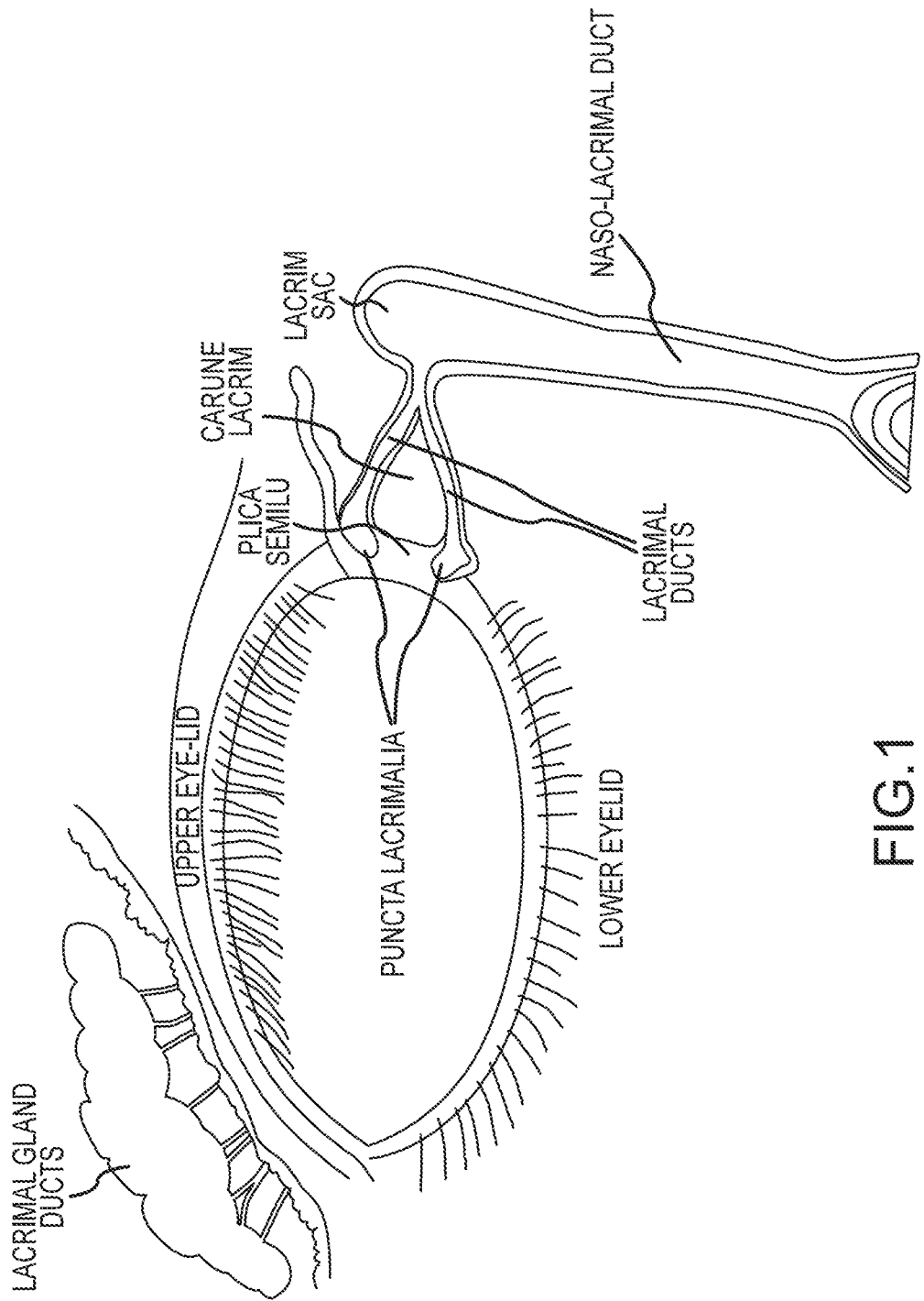
FIG. 1 is an illustration of a typical person's lacrimal system.

The present invention generally relates to a medicament delivery device and, more particularly, to an implantable drug delivery device for delivering a drug to the eye through the lacrimal duct.

Referring to the drawings in detail, wherein like reference numerals indicate like elements throughout, there is shown in FIGS. 2-17 drug delivery devices, generally designated 20, 80, 88, 100, 110, 116, 126, and 138 in accordance with first through eighth exemplary embodiments of the present invention, respectively.

Figure 2:
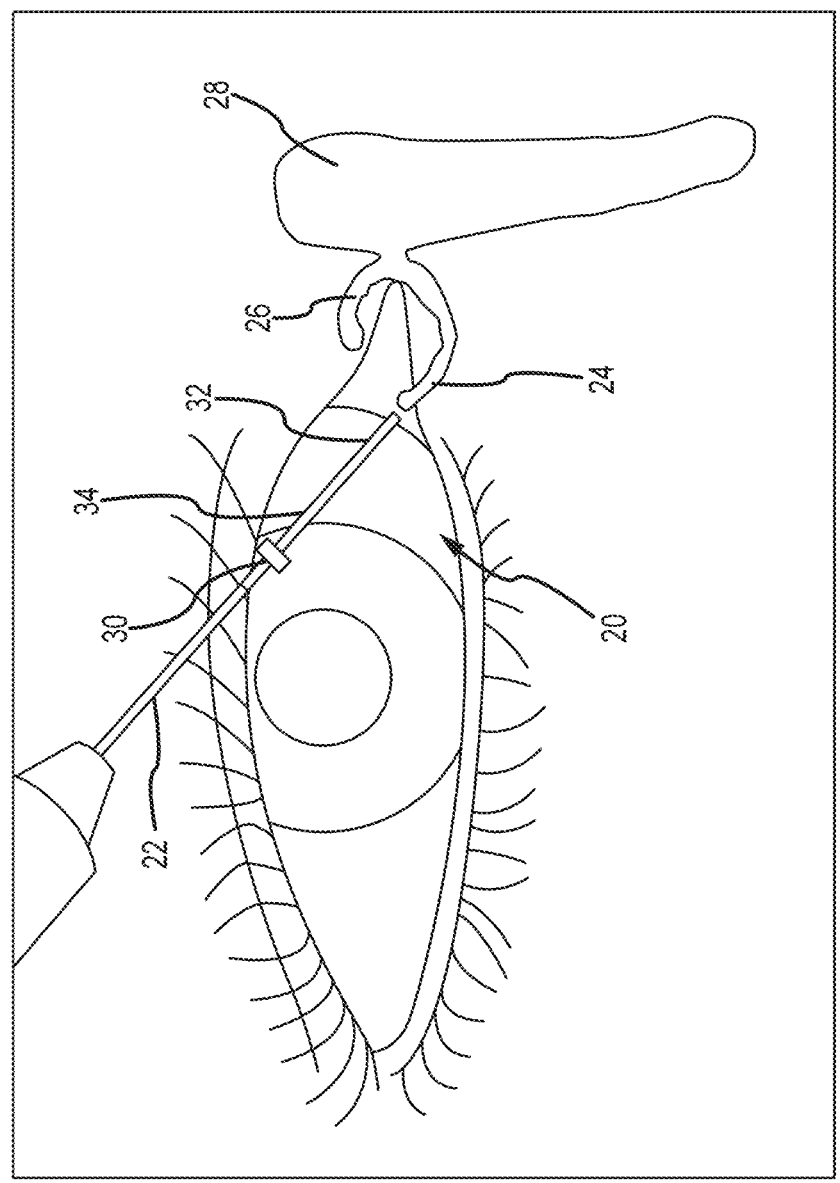
FIG. 2 is a front view of a drug delivery device and delivery guide in accordance with a first exemplary embodiment of the present invention being inserted into a lacrimal duct.
Figure 3:
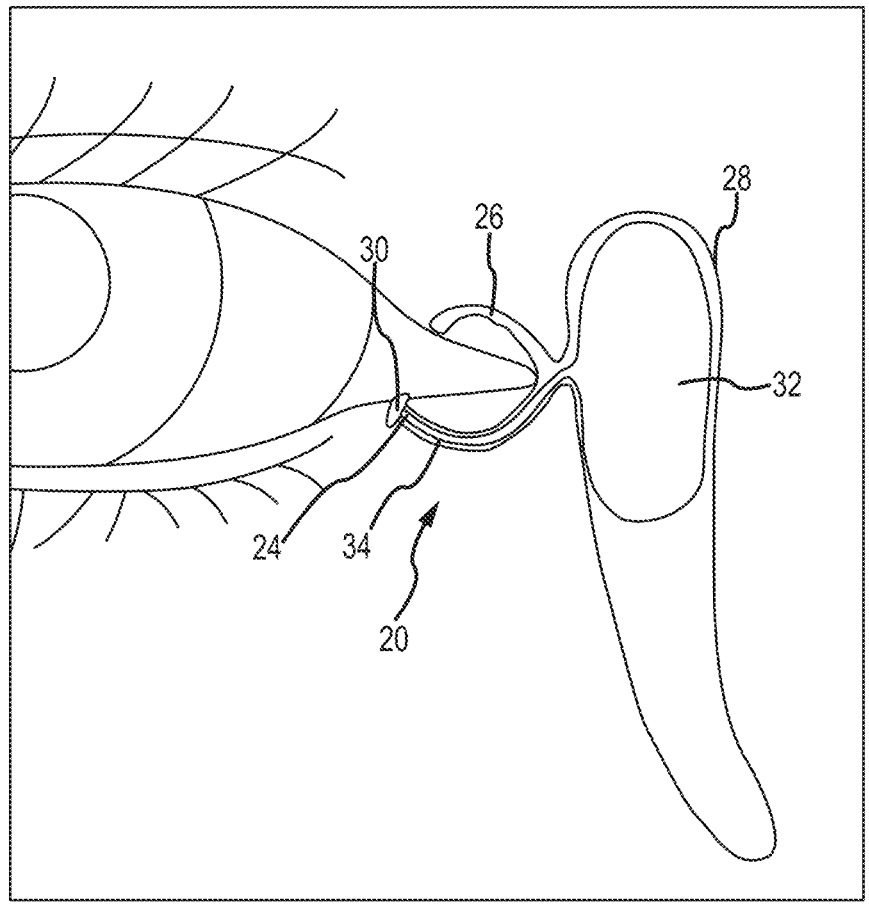
FIG. 3 is a front partial sectional view of the drug delivery device and delivery guide of FIG. 2 inserted in the lacrimal duct with the reservoir in an expanded state.

Referring to FIGS. 2-3, a first exemplary embodiment of the drug delivery device 20 is shown. The drug delivery device 20 may be implanted through a punctum 24 and lacrimal duct 26 of a patient, and into the lacrimal sac 28. In one embodiment, the drug delivery device 20 is inserted in the relaxed state 40 as best seen in FIG. 2. The drug delivery device may be inserted using a delivery guide 22. In some embodiments, the delivery guide 22 moves a reservoir 32 of the drug delivery device 20 from the relaxed state 40 (FIG. 2) to the expanded state (FIG. 3). Once the drug delivery device 20 is implanted and the delivery guide 22 is detached, a face plate 30 may remain at the opening of the punctum to deliver medicament at a delivery site such as an eye. In other embodiments, the drug delivery device 20 may be implanted into other portions of the anatomy such as the nasolacrimal duct, etc.

Referring to FIG. 4, the drug delivery device 20 may include a connector 34 fluidly connecting the reservoir 32 to the face plate 30. In one embodiment, the connector 34 is a connector and includes a lumen. In another embodiment, the connector is a wick. In one embodiment, the connector is a wick and does not include a lumen. The reservoir 32 may be manufactured from a soft, biocompatible material that minimizes or eliminates any tissue damage during insertion of the device or negative interactions with the host site once implanted. In one embodiment, the reservoir 32 is expandable to between 200% to 400% of its size in the relaxed state to hold a quantity of the drug as explained in below. In another embodiment, the reservoir is expandable to between 200% to 1000% of its size in the relaxed state. In another embodiment, the reservoir 32 is expandable to between 275-325% of its size in the relaxed state. In yet another embodiment, the reservoir 32 is expandable to between 300% to 500% of its size in the relaxed state. For example, the reservoir 32 may have a relaxed diameter Rd (see FIG. 6) of about 0.25-1.5 mm and an expanded diameter Ed (see FIG. 7) of about 3.0-6.0 mm. The length of the reservoir 32 may also change as the reservoir moves from the relaxed state 40 to the expanded state 42. For example, the length of the reservoir 32 may expand from 5 mm in the relaxed state to about 30 mm in the expanded state. The reservoir 32 may be maneuvered through the lacrimal duct 26 and into the lacrimal sac 28 because the relatively smaller size in the relaxed state 40 makes the device easier to maneuver. The reservoir 32 may be moved from the relaxed state 40 to the expanded state 42 once it is in the lacrimal sac 28, as explained in greater detail below. Alternatively, the reservoir 32 could be positioned within the lacrimal duct 26 and need not be positioned in the lacrimal sac 28, if desired. The reservoir 32 in FIGS. 6-7 has an internal chamber 44 configured to hold a drug or liquid medicament to be delivered at a delivery site (via elution, pressure induced flow, wicking, etc.). In one embodiment, the chamber 44 holds between about 100-41,000 μL of the drug in the expanded state. In another embodiment, the chamber 44 holds about 300 μL of the drug in the expanded state. The reservoir 32 may be comprised of a material that does not interact with the drug and does not allow the drug to escape from the reservoir 32 (e.g. silicone, thermoplastic elastomer). For example, the reservoir may retain the drug with less than 3% loss of fluid mass over 90 days and the concentration of the drug may be maintained for at least 5 days. The material selected for the reservoir 32 may have elastic properties similar to that of a balloon such that when the reservoir 32 is in the expanded state 42, the elasticity of the reservoir 32 provides a force to dispel the drug from the internal chamber 44 with a relatively low and flat pressure curve to provide a consistent and predictable flow rate of the drug. The reservoir material and geometry may also prevent bursting of the reservoir 32 and allow the reservoir 32 to be re-loaded, if desired.

Figure 7:
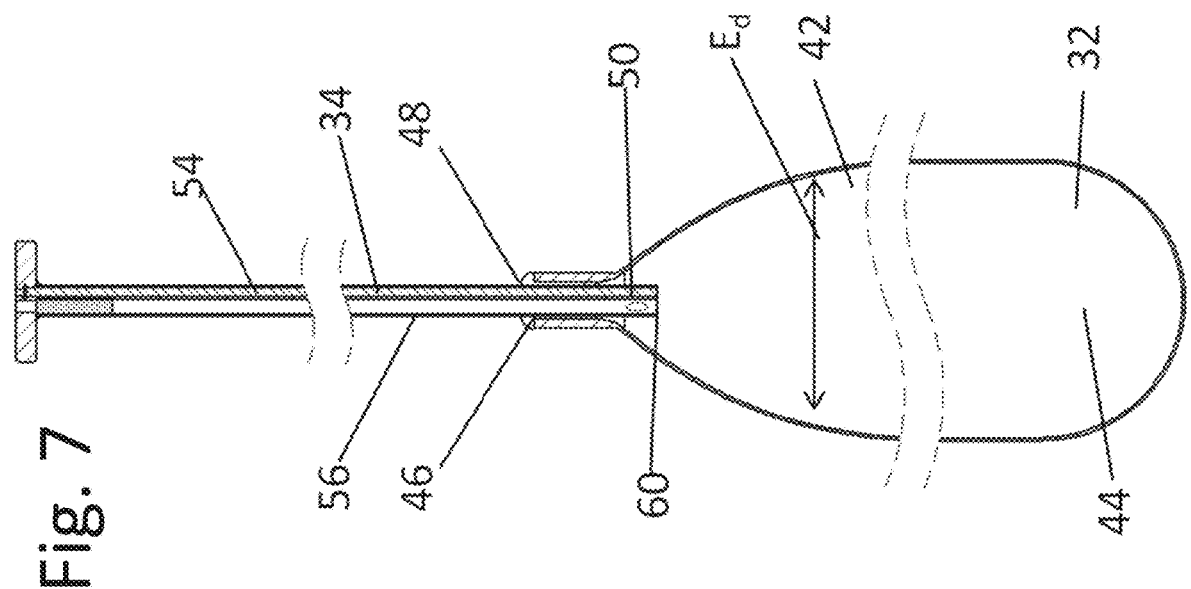
FIG. 7 is a front sectional view of the connector and reservoir of FIG. 2 in an expanded state.
Figure 6:
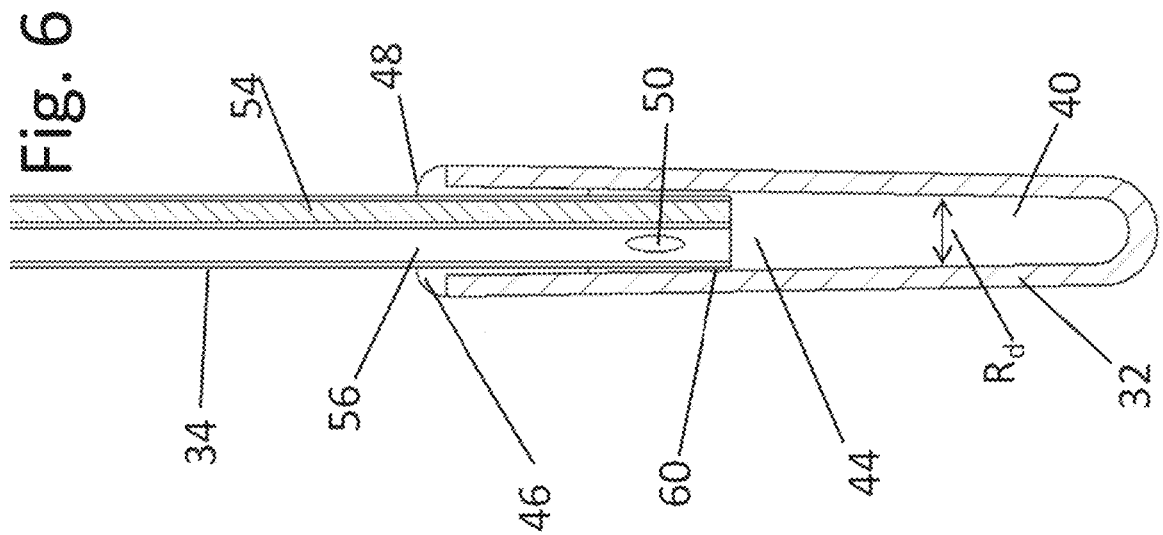
FIG. 6 is a front sectional view of the connector and reservoir of FIG. 2 in a relaxed state.

Referring now to FIGS. 6 and 7, the reservoir 32 may have an opening 46 configured to receive the connector 34. The connector 34 may be inserted through the opening 46 and extend at least partially into the internal chamber 44 such that a rim 48 of the reservoir 32 is above a port 50 on the connector 34. In one embodiment, the reservoir 32 and connector 34 may be manufactured as a monolithic element or coupled via adhesive, welding, etc. such that the connector 34 need not extend through the opening 46 and into the internal chamber 44. In another embodiment, the reservoir 32 and connector 34 are manufactured monolithically but a portion of the connector 34 still extends into the chamber 44 of the reservoir 32. The external surface 52 of the reservoir 32 may have features (e.g. barbs, spikes, textured surface) that at least partially assist in holding the reservoir 32 within the lacrimal sac 28 or other site at which the reservoir 32 is implanted.

Referring to FIGS. 4-5, the connector 34 may be a generally cylindrical member that fluidly connects the reservoir 32 to the face plate 30. The connector 34 may be manufactured from a similarly soft, flexible, biocompatible material to minimize or eliminate tissue damage during insertion. The connector 34 may include a first lumen 54 and a second lumen 56 as shown in FIG. 4 but could alternatively include a single lumen or more than two lumens, if desired. The first lumen 54 may extend from a proximal end 58 toward a distal end 60 of the connector 34 and is connected to the port 50 to transfer the drug from the reservoir 32 to the face plate 30, which is coupled to the proximal end 58 of the connector 34. Although the port 50 is shown as extending through a sidewall of the connector 34, the port could also be on the distal end 60 of the connector. The port 50 could be a hole, slit valve, etc. A slit valve may be a slit in the material which allows one-way flow of material from the reservoir 32. In other embodiments, the connector 34 includes more than one port 50 or more than one first lumen 54. Although the reservoir 32 and the connector 34 are shown in FIG. 4 as separate elements, they could be manufactured as a single element and even be made from the same material but the connector may be somewhat structurally different (e.g. reinforced, thicker walls) such that the connector 34 does not expand when the reservoir 32 is moved from the relaxed to the expanded state. In yet another alternative, the connector 34 expands lengthwise as the reservoir is expanded, thereby causing the first lumen 54 to constrict and control the flow rate of the drug through the first lumen 54.

Referring to FIG. 9, in some embodiments, the rate of flow of the drug through the connector 34 is at least partially controlled by the first lumen 54. For example, the size of the first lumen 54 may influence the rate of flow as a larger lumen will allow greater flow through the connector. In some embodiments, however, it is more desirable to have a slower flow and thus, a smaller first lumen 54, or at least a lumen with a smaller internal diameter, may be adopted. The first lumen 54 may have baffles or some other structural element within the lumen to slow the flow of the drug. For example, hydrogel 62 may be placed within the first lumen 54 as shown in FIG. 9 at least partially controlling the flow of the drug. Hydrogel 62 may provide an effective way to consistently deliver the drug at a generally constant rate between about 0.1 µL and about 100 µL per day by utilizing the pressure of the reservoir 32 to load the drug into the hydrogel 62 without being as pressure dependent as other types of mechanical flow restrictors. The hydrogel 62 may extend the length of the first lumen 54 or may only extend along a portion thereof. The hydrogel 62 may fill a majority, if not all, of the cross sectional area of the first lumen 54 to ensure the drug flows through the hydrogel 62. In some embodiments, the size of the space in the first lumen 54 may be designed to account for flow of the drug outside of the hydrogel 62. The hydrogel 62 may be in a dry state and not absorbed any of the drug during implantation of the drug delivery device 20. The hydrogel 62 may transition to a wetted state after the device 20 is implanted and the drug is transferred into the reservoir 32 and absorbed by the hydrogel 62. In one embodiment, the transition to the wetted state takes between about 1 and 48 hours to become fully saturated and reach steady state flow. Alternatively, the hydrogel 62 may be pre-wetted prior to implantation of the drug delivery device 20, if desired. In one embodiment, the hydrogel 62 may load, or absorb, the drug and delivers it at a delivery site. In other embodiments, the hydrogel 62 may not absorb the drug but instead merely offer a flow resistance to the flow of the drug wherein the reservoir pressure is the driving force for delivering the drug. The flow resistance of the hydrogel 62 may be altered by changing the chemical composition, cross-linking, or geometrical shape of the hydrogel 62.

Other types of flow restricting elements are also contemplated. For example, valves may be positioned in the first lumen 54 which restrict the flow of the drug. The first lumen 54 may be sealed and relatively small holes may be formed in the end of the lumen through which the drug flows. Tight fitting "leaky" components may also be used (e.g. a threaded screw which allows flow along the threaded connection even when fully seated in a threaded opening). The diameter of the first lumen 54 could also change as the pressure in the reservoir changes such that a higher pressure in the reservoir creates a smaller diameter lumen and a lower pressure creates a larger diameter to provide a consistent flow rate. Non-mechanical flow delivery devices such as a wick could also be adopted.

Referring to FIGS. 4 and 9, in some embodiments, the second lumen 56 extends from the proximal end 58 toward the distal end 60 of the connector and receives the delivery guide 22 which includes a cannula 66. The second lumen 56 may extend completely through the connector 34 to allow the cannula 66 to extend through the connector 34 and into the reservoir 32 during implantation of the drug delivery device 20. The second lumen 56 may be sealed after the delivery guide 22 is removed, as explained in greater detail below.

Referring to FIGS. 5 and 9, the face plate 30 may be coupled to the proximal end 58 of the connector 34. In some embodiments, the connector 34 and the face plate 30 are manufactured monolithically and may be made from the same or different materials. In other embodiments, the connector 34 and face plate 30 are manufactured separately and joined by conventional methods known to one of ordinary skill in the art (e.g. adhesive, welding, fasteners). The face plate 30 may have a single first lumen 54 through which the drug is delivered at the delivery site. In another embodiment, the face plate 30 may include any number of first lumens 54. Furthermore, the number of first lumens 54 in the connector 34 need not necessarily be equal to the number of first lumens 54 in the face plate 30 and channels (not shown) may be formed within the face plate 30 to fluidly connect the first lumens 54 of the connector 34 to those of the face plate 34. The second lumen 56 in the face plate 30 may align with the second lumen 56 in the connector 34 to allow the delivery guide 22 to extend through the face plate 30 and into the connector 34. The face plate 30 may have an outer diameter larger than that of the connector 34 such that when the drug delivery device is implanted in the lacrimal system, the connector 34 enters the lacrimal duct 26 but the face plate 30 is prevented from entering the lacrimal duct which helps prevent dislodgement of the drug delivery device 20.

Referring to FIG. 4, the delivery guide 22 may be inserted into the second lumen 56 through the face plate 30 and connector 34, and into the reservoir 32. The delivery guide 22 may include the cannula 66 which may comprise a guide wire which gives rigidity to the drug delivery device 20 as it is being implanted. In another embodiment, the cannula 66 comprises a flexible cannula or a semi-flexible cannula (not shown) which is navigated through the lacrimal duct 26 and into the lacrimal sac 28 after which the drug delivery device 20 is implanted through the cannula. In some embodiments, the cannula 66 is a conduit and delivers the drug into the reservoir 32 after implanting the drug delivery device 20, thereby moving the reservoir 32 from the relaxed state 40 to the expanded state 42.

Figure 10:
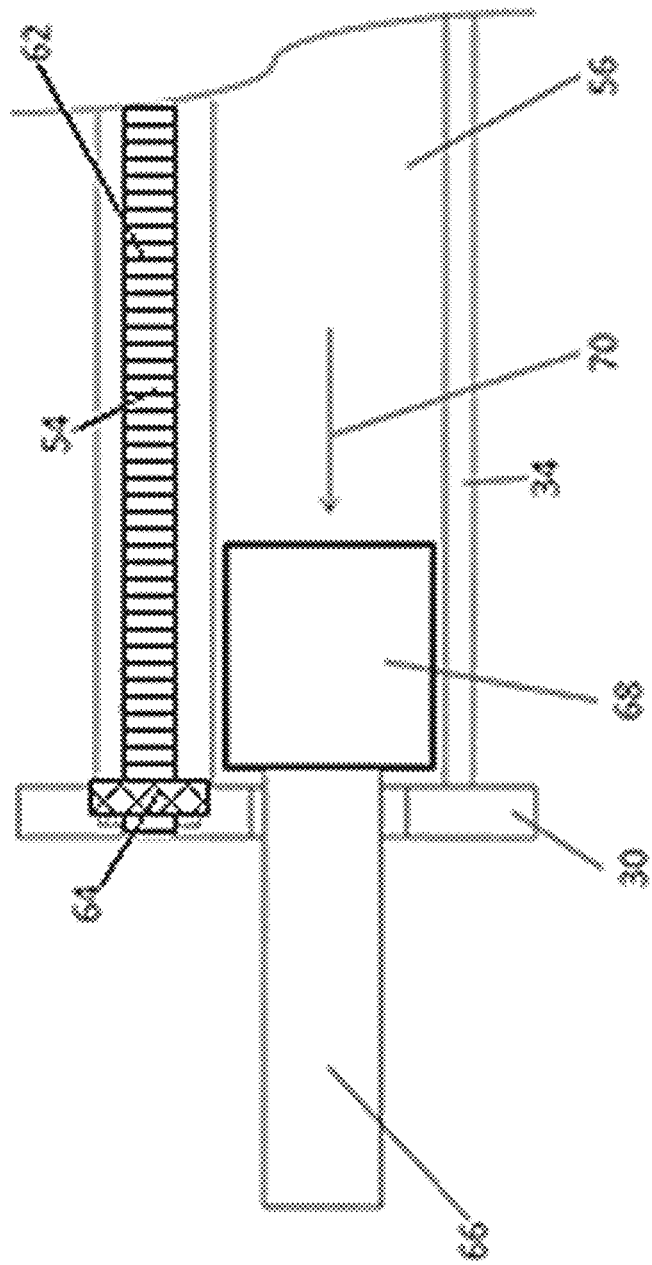
FIG. 10 is a side sectional view of the faceplate and connector of FIG. 2 with a plug in the connector.

Referring to FIG. 10, in one embodiment, a plug 68 is attached to the end of the cannula 66. The plug 68 may be sized and configured to seal the second lumen 56 after the drug delivery device 20 is implanted. The plug 68 may be detachably coupled to the cannula 66 via adhesive, threaded connection, ball and detent structure, etc. and positioned within the distal end 60 of the connector 34 or in the reservoir 32 while the drug delivery device 20 is being implanted. The cannula 66 may pull the plug 68 along the second lumen 56 as the cannula 66 is removed from the delivery device 20 until the plug 68 is adjacent the face plate 30. The plug 68 could also be positioned at any location along the second lumen 56 desired, including at the distal end 60. The drug may exert a force 70 on the plug 68 because the drug is under pressure in the reservoir 32 as previously described and may maintain the position of the plug 68 to effectively seal the second lumen 56. The cannula 66 may be detached from the plug 68 and removed from the drug delivery device 20 after the plug 68 is positioned at the desired location.

In some embodiments, a membrane filter 64 is positioned within the first lumen 54 of the face plate 30. The membrane filter 64 may seal the hydrogel 62 within the first lumen 54 and form a protective barrier preventing contamination of the hydrogel 62 from external substances. The membrane filter 64 may also provide flow control of the drug through the first lumen 54. For example, the porosity of the membrane filter 64 could be such that it restricts flow of the drug. Although the membrane filter 64 is shown as within the face plate 30, it could also be positioned within the first lumen 54, if desired. Furthermore, the entire face plate 30 may be formed of the membrane filter 64, if desired.

Referring to FIG. 11, there is shown a second exemplary embodiment of the drug delivery device, generally designated 80. The drug delivery device 80 may be similar to the first embodiment of the drug delivery device 20 except that the composition of the hydrogel 82 is different. The hydrogel 82 may include a first section 84 adjacent the reservoir 32 and a second section 86 opposite the first section 84. The first section 84 may have a composition which allows for faster absorption of the drug than the second section 86. Therefore, the drug may be quickly absorbed by the first section 84 but delivered by the second section 86 at a relatively slower rate. This configuration helps to control the flow rate of the drug through the drug delivery device 80. Alternatively, the composition of the first and second sections 84, 86 may be reversed such that the first section 84 absorbs the drug more slowly than the second section but the resulting control of the flow rate of the drug is still the same. The first section 84 may have a different chemical composition than the second section 86. The first and second sections 84, 86 may have the same chemical composition but the first section 84 may be more densely packed than the second section 86 such that the porosity of the first section 84 is different than the porosity of the second section 86. For example, the first section 84 may have a larger porosity than the second section 86 and the larger porosity allows a faster flow rate of the drug.

Referring to FIG. 12, there is shown a third exemplary embodiment of the drug delivery device, generally designated 88. The first lumen 90 may include a first portion 92 having a first diameter and a second portion 94 having a second diameter different than the first diameter. The first portion 92 may have a greater diameter than the second portion 94 and the hydrogel 62 may fill both the first portion 92 and the second portion 94. The increased amount of hydrogel 62 in the first portion 92 may allow the drug to be absorbed faster by the first portion 92 than the second portion 94. Thus, the relative size of the first portion 92 to the second portion 94 may help control the rate of flow of the drug. Furthermore, the composition of the hydrogel 62 in the first portion 92 and the second portion 94 may be the same or may be different from each other as described with respect to other embodiments. The demarcation between the first portion 92 and second portion 94 may form a shoulder 96, but the transition could also be a gradual change giving the first lumen 90 a frustoconical shape.

Referring to FIG. 13, there is shown a fourth exemplary embodiment of the drug delivery device, generally designated 100. The drug delivery device 100 is similar to the first embodiment of the drug delivery device 20 except that the composition of the hydrogel 102 is different. The hydrogel 102 may include a hydrophilic portion 104 and a hydrophobic portion 106. The hydrophilic and hydrophobic portions 104, 106 may have different characteristics (e.g. physical makeup, chemical properties) such that the hydrophilic portion 104 absorbs and delivers the drug faster than the hydrophobic portion 106. The hydrophilic portion 104 may extend substantially from the distal end 60 of the connector 34 to the proximal end 58 such that the drug is delivered through the hydrophilic portion 104 along a defined path (e.g. helical, straight line). The ratio of the hydrophilic portion 104 to the hydrophobic portion 106 may be the same throughout the first lumen 54 or may be greater at the distal end 60 than at the proximal end 58 such that the drug is absorbed by the hydrogel more quickly than it is delivered. Alternatively, the hydrophilic portion 104 and hydrophobic portion 106 need not be homogenous portions as shown in FIG. 13. Instead, the hydrogel 102 may be a heterogeneous substance with the ratio of hydrophilic elements greater at the distal end 60 than at the proximal end 58.

Referring to FIG. 14, there is shown a fifth exemplary embodiment of the drug delivery device, generally designated 110. The drug delivery device 110 is similar to the first embodiment of the drug delivery device 20 except that the drug delivery device 110 includes drug containing spheres 112 and does not include any hydrogel although hydrogel as previously described could be included, if desired. The spheres 112 are within the reservoir 32 when the drug delivery device 110 is implanted. After the drug delivery device 110 is implanted as previously described, a liquid (e.g. saline, liquid medicament, water) may be injected through the delivery guide 22 and into the reservoir where it washes away the spheres 112 and the drug within the spheres 112 is delivered over time through the connector and lumen to deliver the drug at the delivery site.

Referring to FIG. 15, there is shown a sixth exemplary embodiment of the drug delivery device, generally designated 116. The drug delivery device 116 is similar to the first embodiment of the drug delivery device 20 except that the drug delivery device 116 includes only a single lumen 118 in the connector 120. The hydrogel 62 may not be in the lumen 118 when the device 116 is implanted. Instead, the hydrogel 62 may be coupled to the end of the cannula 66 and pulled into the lumen 118 as the cannula 66 is being removed from the connector 120. Adhesive 122 may be positioned on the proximal end 58 of the connector 120 such that the hydrogel 62 is at least partially secured within the connector 120 by adhesive 122 in addition to the pressure exerted by the drug from the reservoir (not shown). The adhesive 122 may also secure the face plate (not shown) to the connector 120. The hydrogel 62 may control the flow rate of the drug and also seal the lumen 118.

Referring to FIG. 16, there is shown a seventh exemplary embodiment of a face plate, generally designated 126. The face plate 126 is similar to the face plate 30 except that the face plate 126 includes a connector 128 and a barb 130. The barb 130 may secure the face plate 126 within the first lumen 54 via an interference fit. The barb 130 may be manufactured from a material such as rubber, silicone, etc. that allows the barb 130 to slightly deform when it enters the first lumen 54 and secures the face plate 126 therein. The face plate 126 may include an end piece 132 with multiple openings 134 through which the drug is delivered. Of course, the face plate 126 may also include only a single opening 134 in the end piece 132. The connector 128 may include the hydrogel 62 or membrane filter 64 as previously described. The face plate 126 may be used with a connector 34 having a single lumen wherein the barb 130 seals the lumen and the drug flows through hydrogel within the connector and out of the face plate. Alternatively, the face plate 126 may be used with a connector 34 having two lumens wherein the face plate 126 is secured within the first lumen.

Referring to FIG. 17, there is shown an eighth exemplary embodiment of a drug delivery device, generally designated 138. The drug delivery device 138 is similar to the drug delivery device 20 of the first embodiment except that the drug delivery device 138 includes a valve 140 sealing the second lumen 56 instead of a plug 68. The valve 140 may be moveable between an open position 142 and a closed position 144 (shown in phantom in FIG. 17). The valve 140 may be any type of valve (e.g. duck bill valve, flap valve, one-way valve) provided that the valve 140 allows the cannula 66 to be inserted into the second lumen 56 and seals the second lumen 56 when the cannula 66 is removed. The valve 140 may be secured in the closed position by the pressure of the drug within the second lumen 56 after the cannula 66 delivers the drug into the reservoir 32 and is removed. The valve 140 may allow the cannula 66 to be reinserted to introduce an additional volume of the drug into the reservoir 32 such that the drug delivery device 138 is re-useable.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "right", "left", "lower" and "upper" designate directions in the drawings to which reference is made. The words "inwardly" and "outwardly" refer to directions toward and away from, respectively, the geometric center of the drug delivery device. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art may readily appreciate that the steps may be varied and still remain within the spirit and scope of the present invention.

What is claimed is:

1. A lacrimal drug delivery device comprising:
 a reservoir configured to hold a therapeutic agent, the reservoir configured to transition between a relaxed state and an expanded state;
 a delivery guide;
 a connector comprising:
  a first lumen in fluid communication with the reservoir and configured to deliver the therapeutic agent from the reservoir to an eye of a subject;
  a second lumen in fluid communication with the reservoir and configured to receive the delivery guide therein to deliver the therapeutic agent into the reservoir;
 a hydrogel disposed within the first lumen and configured to control a flow rate of the therapeutic agent from the reservoir to the eye; and
 a plug releasably couplable to the delivery guide, the plug configured to release from the delivery guide and seal the second lumen to prevent the therapeutic agent from flowing through the second lumen after the delivery guide delivers the therapeutic agent into the reservoir.

2. The lacrimal drug delivery device of claim 1, further comprising the therapeutic agent.

3. The lacrimal drug delivery device of claim 1, further comprising a faceplate at a proximal end of the connector.

4. The lacrimal drug delivery device of claim 1, wherein, when the therapeutic agent is delivered into the reservoir, the reservoir transitions from the relaxed state to the expanded state; wherein, when the therapeutic agent is delivered to the eye, the reservoir transitions from the expanded state to the relaxed state.

5. The lacrimal drug delivery device of claim 1, wherein, when the reservoir is in the expanded state, the reservoir applies a constant force onto the therapeutic agent such that the therapeutic agent flows from the reservoir at a consistent flow rate.

6. The lacrimal drug delivery device of claim 1, wherein an internal chamber of the reservoir defines a relaxed diameter when the reservoir is in the relaxed state and an expanded diameter when the reservoir is in the expanded state, wherein the relaxed diameter is between 0.25 mm and 1.5 mm, wherein the expanded diameter is between 3.0 mm and 6.0 mm.

7. The lacrimal drug delivery device of claim 1, wherein the first lumen is formed in the connector and the second lumen is formed in the connector.

8. The lacrimal drug delivery device of claim 1, wherein the plug is configured to release from the delivery guide and seal the second lumen as the delivery guide is removed from the second lumen.

9. The lacrimal drug delivery device of claim 1, wherein the plug is releasably coupled to the delivery guide via at least one of an adhesive, a threaded connection, or a ball and detent structure.

10. A method for inhibiting onset of an ocular disease in the eye of the subject in need thereof, the method comprising:
    implanting the lacrimal drug delivery device of claim 1 into the eye of the subject;
    delivering the therapeutic agent into the reservoir through the second lumen of the lacrimal drug delivery device;
    sealing the second lumen with the plug; and
    delivering the therapeutic agent through to the eye of the subject through the first lumen of the lacrimal drug delivery device.

11. The method of claim 10, wherein implanting the lacrimal drug delivery device comprises inserting the lacrimal drug delivery device through a punctum of the eye of the subject such that the reservoir is within a lacrimal sac of the eye of the subject and the connector is within a lacrimal duct of the eye of the subject; wherein the reservoir is in the relaxed state during implanting; wherein the reservoir transitions from the relaxed state to the expanded state when the therapeutic agent is delivered into the reservoir through the second lumen.

12. A lacrimal drug delivery device comprising:
    a reservoir configured to hold a therapeutic agent, the reservoir configured to transition between a relaxed state and an expanded state;
    a connector comprising:
    a first lumen in fluid communication with the reservoir and configured to deliver the therapeutic agent from the reservoir to an eye of a subject;
    a second lumen in fluid communication with the reservoir and configured to receive a delivery guide therein to deliver the therapeutic agent into the reservoir;
    a hydrogel disposed within the first lumen and configured to control a flow rate of the therapeutic agent from the reservoir to the eye;
    a plug provided in the second lumen and configured to be releasably couplable to the delivery guide; and
    the delivery guide including a guide wire having an opening therethrough, the delivery guide removably positionable within the second lumen, wherein, when the delivery guide is positioned in the second lumen, the delivery guide is removably couplable to the lacrimal drug delivery device to implant the lacrimal drug delivery device into the eye of the subject, wherein, when the delivery guide is positioned in the second lumen, the delivery guide is configured to deliver the therapeutic agent through the opening and into the reservoir such that the reservoir transitions from the relaxed state to the expanded state, wherein, when the plug is releasably coupled to the delivery guide, the delivery guide is configured to release the plug to seal the second lumen.

13. The lacrimal drug delivery device of claim 12, further comprising the therapeutic agent.

14. The lacrimal drug delivery device of claim 12, further comprising a faceplate at a proximal end of the connector.

15. The lacrimal drug delivery device of claim 12, wherein, when the therapeutic agent is delivered into the reservoir, the reservoir transitions from the relaxed state to the expanded state; wherein, when the therapeutic agent is delivered to the eye, the reservoir transitions from the expanded state to the relaxed state.

16. The lacrimal drug delivery device of claim 12, wherein, when the reservoir is in the expanded state, the reservoir applies a compressive force onto the therapeutic agent such that the therapeutic agent flows from the reservoir at a consistent flow rate.

17. The lacrimal drug delivery device of claim 12, wherein an internal chamber of the reservoir defines a relaxed diameter when the reservoir is in the relaxed state and an expanded diameter when the reservoir is in the expanded state, wherein the relaxed diameter is between 0.25 mm and 1.5 mm, wherein the expanded diameter is between 3.0 mm and 6.0 mm.

18. The lacrimal drug delivery device of claim 12, wherein the delivery guide is configured to release the plug to seal the second lumen after the delivery guide delivers the therapeutic agent through the opening and into the reservoir.

19. A method for inhibiting onset of an ocular disease in the eye of the subject in need thereof, the method comprising:
    implanting the lacrimal drug delivery device of claim 12, with the delivery guide removably coupled to the second lumen, into the eye of the subject;
    delivering the therapeutic agent, with the delivery guide, into the reservoir through the second lumen of the lacrimal drug delivery device; and
    delivering the therapeutic agent through to the eye of the subject through the first lumen of the lacrimal drug delivery device.

20. The method of claim 19, wherein implanting the lacrimal drug delivery device comprises inserting the lacrimal drug delivery device through a punctum of the eye of the subject such that the reservoir is within a lacrimal sac of the eye of the subject and the connector is within a lacrimal duct of the eye of the subject; wherein the reservoir is in the relaxed state during implanting; wherein the reservoir transitions from the relaxed state to the expanded state when the therapeutic agent is delivered into the reservoir through the second lumen.

* * * * *

UNITED STATES PATENT AND TRADEMARK OFFICE
CERTIFICATE OF CORRECTION

PATENT NO. : 12,011,390 B2
APPLICATION NO. : 17/524610
DATED : June 18, 2024
INVENTOR(S) : Andrew Schieber et al.

Page 1 of 1

It is certified that error appears in the above-identified patent and that said Letters Patent is hereby corrected as shown below:

In the Claims

- In Claim 10, Column 19, Line 35, insert --at least a portion of-- after 'delivering'.

- In Claim 19, Column 20, Line 51, insert --at least a portion of-- after 'delivering'.

Signed and Sealed this
Twenty-sixth Day of November, 2024

Katherine Kelly Vidal
*Director of the United States Patent and Trademark Office*